United States Patent
Lei et al.

(10) Patent No.: US 8,917,779 B2
(45) Date of Patent: Dec. 23, 2014

(54) ELECTROCARDIOGRAM SIGNAL COMPRESSION AND DE-COMPRESSION SYSTEM

(71) Applicant: National Cheng Kung University, Tainan (TW)

(72) Inventors: Sheau-Fang Lei, Tainan (TW); Shin-Chi Lai, Taichung (TW); Chien-Sheng Lan, Taoyuan County (TW)

(73) Assignee: National Cheng Kung University, Tainan (TW)

( * ) Notice: Subject to any disclaimer, the term of this patent is extended or adjusted under 35 U.S.C. 154(b) by 142 days.

(21) Appl. No.: 13/795,845

(22) Filed: Mar. 12, 2013

(65) Prior Publication Data

US 2013/0243105 A1 Sep. 19, 2013

(30) Foreign Application Priority Data

Mar. 16, 2012 (TW) .............................. 101109081 A

(51) Int. Cl.
- H04B 1/66 (2006.01)
- H04L 29/08 (2006.01)
- H03M 7/30 (2006.01)
- G06F 19/00 (2011.01)

(52) U.S. Cl.
CPC ....... H04L 29/08792 (2013.01); H03M 7/3059 (2013.01); *G06F 19/36* (2013.01)

USPC ............ 375/241; 375/240; 375/340; 600/508

(58) Field of Classification Search
CPC ...................... H03M 7/3059; H04L 29/08792
USPC ......... 375/241, 240, 242, 244, 245, 246, 253, 375/340

See application file for complete search history.

(56) References Cited

U.S. PATENT DOCUMENTS

| | | | | |
|---|---|---|---|---|
| 8,548,574 B2* | 10/2013 | Wang | | 600/509 |
| 8,632,465 B1* | 1/2014 | Brockway | | 600/300 |
| 8,731,081 B2* | 5/2014 | Mittal et al. | | 375/260 |

* cited by examiner

*Primary Examiner* — Kabir A Timory
*Assistant Examiner* — David S Huang
(74) *Attorney, Agent, or Firm* — Bacon & Thomas, PLLC

(57) ABSTRACT

The invention provides an electrocardiogram signal compression and de-compression system. The invention uses the sign characteristics of the coefficients of the discrete cosine transform type IV and the characteristics of quantization of spectrum to perform the differential pulse code modulation of the spectrum for preserving the high frequency characteristics of the spectrum of the discrete Fourier transform. The invention also uses the Huffman coding to increase the compression ratio. Different from the conventional compression technology, the invention uses the fact that the quantization values of the spectrum in the high frequency are almost the same to increase the compression ratio and preserve the characteristics of high frequency components of the spectrum.

16 Claims, 31 Drawing Sheets

Pseudo code:
```
for k = 0~63
    SUM_COS = 0;
        for n = 0~63
            COSINE = cos(((2*n+1)*(2*k+1)*pi)/(4*N));
            SUM_COS = SUM_COS +  COSINE ;
        end
    COEFFICIENT(k) = SUM_COS;
end
```

| Difference bit number | Difference |
|---|---|
| 0 | 0 |
| 1 | -1, 1 |
| 2 | -3,-2, 2,3 |
| 3 | -7~-4, 4~7 |
| 4 | -15~-8, 8~15 |
| 5 | -31~-16, 16~31 |
| 6 | -63~-32, 32~63 |
| 7 | -127~-64, 127~64 |
| 8 | -255~-128, 128~255 |
| 9 | -511~-256, 256~511 |
| 10 | -1023~-512, 512~1023 |
| 11 | -2047~-1024, 1024~2047 |

FIG. 13

| Difference bit number | Occurrence probability | Huffman table |
|---|---|---|
| 0 | 0.432849977 | 1 |
| 1 | 0.320305796 | [0,0] |
| 2 | 0.0971258 | [0,1,1] |
| 3 | 0.051367421 | [0,1,0,0,0] |
| 4 | 0.033346082 | [0,1,0,1,0] |
| 5 | 0.025445549 | [0,1,0,1,1] |
| 6 | 0.016620287 | [0,1,0,0,1,1] |
| 7 | 0.010190705 | [0,1,0,0,1,0,1,0] |
| 8 | 0.012222603 | [0,1,0,0,1,0,0] |
| 9 | 0.000460276 | [0,1,0,0,1,0,1,1,0] |
| 10 | 5.71E-05 | [0,1,0,0,1,0,1,1,1,0] |
| 11 | 8.35E-06 | [0,1,0,0,1,0,1,1,1,1] |

FIG. 14

| Difference bit number a | Huffman code number b | Total bit number of difference coding a+b | Occurrence probability |
|---|---|---|---|
| 0 | 1 | 1 | 0.432849977 |
| 1 | 2 | 3 | 0.320305796 |
| 2 | 3 | 5 | 0.0971258 |
| 3 | 5 | 8 | 0.051367421 |
| 4 | 5 | 9 | 0.033346082 |
| 5 | 5 | 10 | 0.025445549 |
| 6 | 6 | 12 | 0.016620287 |
| 7 | 8 | 15 | 0.010190705 |
| 8 | 7 | 15 | 0.012222603 |
| 9 | 9 | 18 | 0.000460276 |
| 10 | 10 | 20 | 5.71E-05 |
| 11 | 10 | 21 | 8.35E-06 |

FIG. 15

| Difference bit number | Difference | |
|---|---|---|
| 0 | 0 | |
| 1 | -1 | 1 |
| 2 | -3,-2 | 2,3 |
| 3 | -7~-4 | 4~7 |
| 4 | -15~-8 | 8~15 |
| 5 | -31~-16 | 16~31 |
| 6 | -63~-32 | 32~63 |
| 7 | -127~-64 | 127~64 |
| 8 | -255~-128 | 128~255 |
| 9 | -511~-256 | 256~511 |
| 10 | -1023~-512 | 512~1023 |
| 11 | -2047~-1024 | 1024~2047 |

FIG. 17

| Difference bit number | Occurrence probability | Huffman table |
|---|---|---|
| 0 | 0.567578574 | 0 |
| 1 | 0.022478664 | [1,1,1,1,0] |
| 2 | 0.004780075 | [1,0,0,1,1,1,1] |
| 3 | 0.006647998 | [1,0,0,1,1,1,0] |
| 4 | 0.006850074 | [1,1,1,1,1,1] |
| 5 | 0.011087518 | [1,1,1,1,1,0] |
| 6 | 0.017198014 | [1,0,0,1,1,0] |
| 7 | 0.032534261 | [1,0,0,1,0] |
| 8 | 0.054640571 | [1,1,1,0] |
| 9 | 0.103813803 | [1,1,0] |
| 10 | 1.09E-01 | [1,0,1] |
| 11 | 6.35E-02 | [1,0,0,0] |

FIG. 18

| Difference | −7 | −6 | −5 | −4 | 4 | 5 | 6 | 7 |
|---|---|---|---|---|---|---|---|---|
| Difference table address with difference bit number = 3 | 000 | 001 | 010 | 011 | 100 | 101 | 110 | 111 |

FIG. 19

| Difference bit number a | Huffman code number b | Total bit number of difference coding a+b | Occurrence probability |
|---|---|---|---|
| 0 | 1 | 1 | 0.567578574 |
| 1 | 5 | 6 | 0.022478664 |
| 2 | 7 | 9 | 0.004780075 |
| 3 | 7 | 10 | 0.006647998 |
| 4 | 6 | 10 | 0.006850074 |
| 5 | 6 | 11 | 0.011087518 |
| 6 | 6 | 12 | 0.017198014 |
| 7 | 5 | 12 | 0.032534261 |
| 8 | 4 | 12 | 0.054640571 |
| 9 | 3 | 12 | 0.103813803 |
| 10 | 3 | 13 | 1.09E-01 |
| 11 | 4 | 15 | 6.35E-02 |

FIG. 20

ELECTROCARDIOGRAM SIGNAL COMPRESSION AND DE-COMPRESSION SYSTEM

BACKGROUND OF THE INVENTION

1. Field of the Invention

The present invention relates to the technical field of digital signal processing and, more particularly, to an electrocardiogram signal compression and de-compression system.

2. Description of Related Art

Because the generation of electrocardiogram (ECG) requires continuously recording electrocardiogram signals, typical medical instruments usually do not have enough memory for processing the signals. Taking the existent multi-lead-tapeless ECG Holter system as an example, it uses semiconductor memory as storage media. The semiconductor memory has to store a system program and three ECG signal recordings each for continuous 24 hours. The storage of such data requires a great amount of memory, resulting in high cost for many medical instruments.

Due to the great amount of data and long recording time for ECG, there are lots of ECG signal compressing methods proposed for reducing the cost. As a result, current medical instruments generally use a data compressing method to reduce the cost. By compressing the ECG signals, the memory space can be saved and thus the ECG data can be conveniently added into a central database, so as to perform analysis and comparison data for therapy subsequently. Because the amount of the compressed data is small, it is able to transmit the data in real time via a wired or wireless channel, whereby the prior heart rate monitoring system can be integrated into a portable device to facilitate in monitoring the heart rate of a patient at any time.

FIG. 1 is a schematic diagram illustrating the ECG signals, wherein the important information in the ECG signals focuses on P, Q, R, S and T waveforms, including their positions, shapes, sizes, etc. The P waveform stands for the effect of an atrium (of the heart), in which the left atrium receives the blood full of oxygen from the lung and the right atrium receives the blood without oxygen from the hole body, and this effect continues for about 90 ms. The next part of ECG is QRS-complex waveform, which stands for the effect of a chamber (of the heart), in which the left chamber sends the blood full of oxygen to the whole body and the right chamber sends the blood without oxygen to the lung, and this effect continues for about 80 ms. During the period of time that the QRS-complex waveform appears, the atrium of the heart gradually resumes and prepares to repeat another cycle. During the T waveform, the chamber of the heart also gradually resumes and prepares to repeat another cycle. The time between two adjacent QRS-complex waveforms or R waveforms is a reciprocal of the heartbeat frequency. These data should be reserved to the best no matter what compressing method is used.

The prior art only considers compression of the ECG signals and thus devotes to increasing the compression ratio (CR) of the technique. However, with the advance of the technology, no matter for the flash memory, the dynamic random access memory or the hard disk, the storage capacity has been greatly increased, so that the compression ratio is no longer the major target for ECG compression. In turn, the depression of distortion can provide excellent reconstructed signals for allowing the doctors to make a most correct decision. Therefore, it is desirable to provide an improved electrocardiogram signal compression and de-compression system to mitigate and/or obviate the aforementioned problems.

SUMMARY OF THE INVENTION

The object of the present invention is to provide an electrocardiogram signal compression and de-compression system, which has excellent compression ratio and low distortion rate, as well as excellent quality score after de-compression.

In one aspect of the present invention, there is provided an electrocardiogram signal compression system, which includes: a normalization device for receiving N electrocardiogram signals and performing normalization operation on the N electrocardiogram signals to generate N normalized signals, where N is a positive integer; a discrete cosine transform device connected to the normalization device for receiving the N normalized signals and performing discrete cosine operation to generate N discrete cosine signals; an absolute value and quantization device connected to the discrete cosine transform device for receiving N discrete cosine signals and performing absolute value operation and quantization operation to generate N quantized amplitude signals; a difference coding device connected to the absolute value and quantization device for receiving the N quantized amplitude signals and performing differential pulse code modulation (DPCM) on the N quantized amplitude signals to generate N difference signals; a first variable length coding device connected to the difference coding device for performing variable length coding operation on the N difference signals to generate a first data stream; a sign and difference device connected to the discrete cosine transform device for receiving the N discrete cosine signals and recoding signs of the N discrete cosine signals, so as to generate three sign signals; a second variable length coding device connected to the sign and difference device for performing variable length coding operation on the three sign signals to generate a second data stream; and a mixer connected to the first variable length coding device and the second variable length coding device for mixing the first data stream and the second data stream to generate a compressed electrocardiogram data stream.

In another aspect of the present invention, there is provided an electrocardiogram signal de-compression system includes: a parser device for receiving a compressed electrocardiogram data stream and analyzing the compressed electrocardiogram data stream, so as to generate a first data stream and a second data stream; a first variable length decoding device connected to the parser device for performing variable length decoding operation on the first data stream to generate N difference signals, where N is a positive integer; a difference decoding device connected to the first variable length decoding device for receiving the N difference signals and performing differential pulse code modulation (DPCM) operation on the N difference signals to generate N quantized amplitude signals; an inverse quantization device connected to the difference decoding device for receiving the N quantized amplitude signals and performing inverse quantization operation to generate inverse quantization signals of N discrete cosine signals; a second variable length decoding device connected to the parser device for performing variable length decoding operation on the second data stream to generate three sign and difference signals; a restored difference and sign prediction device connected to the second variable length decoding device for receiving the three sign and difference signals and performing restored difference and sign prediction operation to generate signs of the N discrete cosine signals; an inverse discrete cosine transform device connected to the inverse quantization device and the restored difference and sign prediction device for receiving the inverse quantization signals of the N discrete cosine signals and the signs of the N discrete cosine signals to generate the N discrete cosine signals, and performing inverse discrete cosine operation on the N discrete cosine signals so as to generate N normalized signals; and an inverse normalization device connected to the inverse discrete cosine transform device for receiving the N normalized signals and performing inverse normalization operation on the N normalized signals to generate N electrocardiogram signals.

Other objects, advantages, and novel features of the invention will become more apparent from the following detailed description when taken in conjunction with the accompanying drawings.

BRIEF DESCRIPTION OF THE DRAWINGS

FIG. 13 shows a difference table in accordance with the present invention;

FIG. 14 shows a Huffman code table in accordance with the present invention;

FIG. 15 schematically illustrates the total bit number of difference coding in accordance with the present invention;

FIG. 17 shows another difference table in accordance with the present invention;

FIG. 18 shows another Huffman code in accordance with the present invention;

FIG. 19 schematically illustrates the difference table address for the difference bit number being 3;

FIG. 20 shows the bit number for sign compression flow in accordance with the present invention;

DETAILED DESCRIPTION OF THE PREFERRED EMBODIMENT

Figure 2:
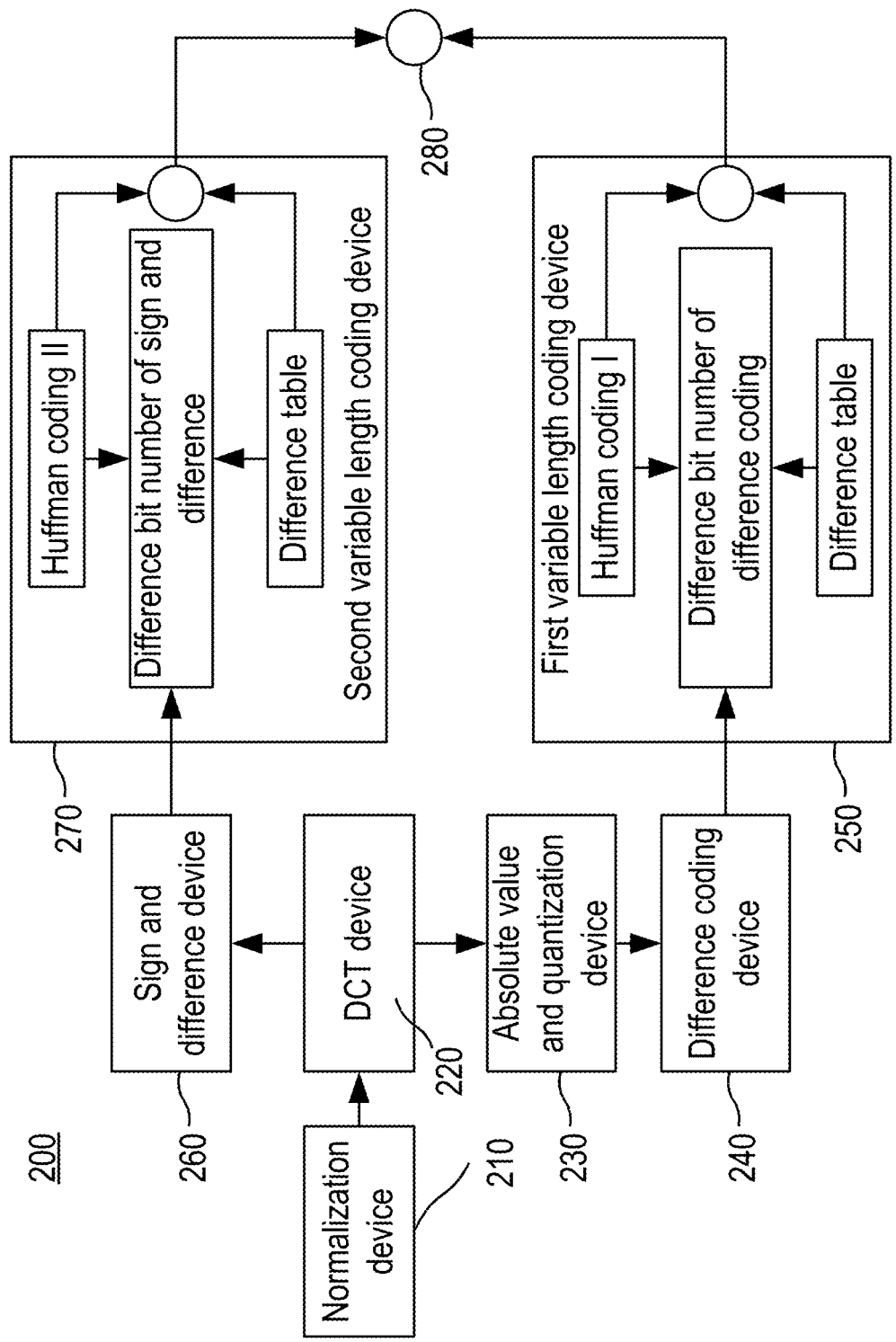
FIG. 2 is a block diagram showing the ECG signal compression system in accordance with a preferred embodiment of the present invention.

FIG. 2 is a block diagram showing the electrocardiogram (ECG) signal compression system 200 in accordance with a preferred embodiment of the present invention. The system 200 includes normalization device 210, a discrete cosine transform (DCT) device 220, an absolute value and quantization device 230, a difference coding device 240, a first variable length coding device 250, a sign and difference device 260, a second variable length coding device 270, and a mixer 280.

Figure 3:
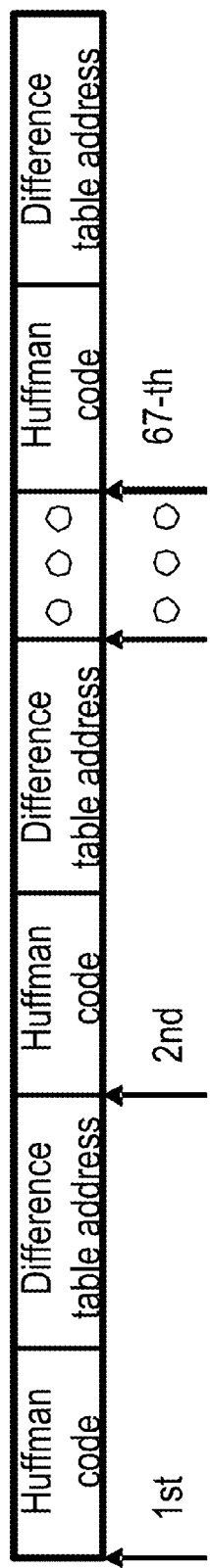
FIG. 3 shows the data format of the compressed bit stream in accordance with the present invention.

There are 64 samples of signals per frame inputted to the ECG signal compression system 200 of the present invention and, after compression, there are 67 compressed bit streams generated for output, each compressed bit stream being composed of Huffman coding and difference table address, wherein three of the compressed bit streams are provided for recording signs and the remaining 64 of the compressed bit streams are the result of the input signals after being transformed and compressed. The data format of the compressed bit stream is shown in FIG. 3.

The normalization device 219 receives N ECG signals for performing a normalization operation on the N ECG signals x(n), where N is a positive integer and, in this embodiment, N is 64.

The normalization device 210 first normalizes the 64 samples of input ECG signals for the purpose of controlling the dynamic range (i.e., the maximum and minimum value) of the coefficient after the discrete cosine transform device 220 perform a DCT-IV operation to be in a smaller range. If no normalization is done, the dynamic range of transformed coefficients will be very large, resulting in requiring more bits for representation.

There are two choices for normalization, one being normalized to −1 to 1 and the other one being normalized to 0 to 1. In the present invention, the normalization device 210 uses the scheme of being normalized to −1 to 1 due to that, after transformation, the present invention has a smaller dynamic range in comparison with the scheme of being normalized to 0 to 1.

Figure 4:
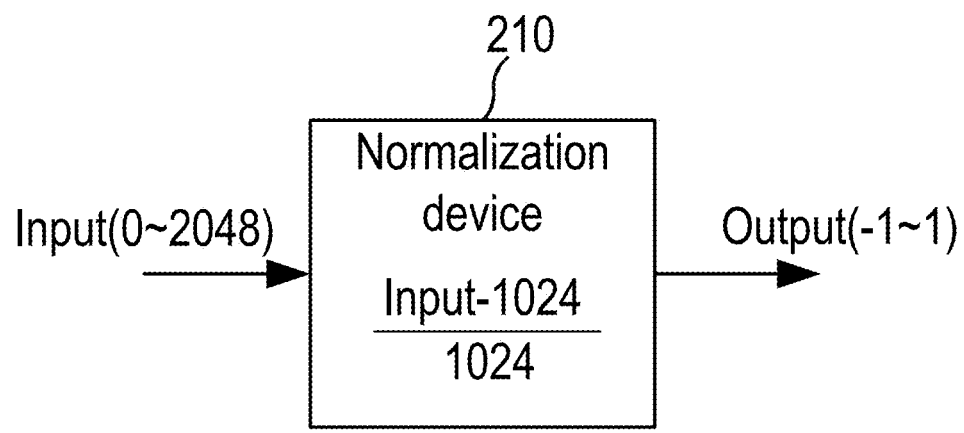
FIG. 4 schematically illustrates the operation of the normalization device in accordance with the present invention.

According to the ECG signals in MIT-BIH database, the value is between 0 and 2048 and thus, if it is to be normalized to −1 to 1, the original signal has to be minus 1024 and then divided by 1024, as shown in FIG. 4. FIG. 4 schematically illustrates the operation of the normalization device 210 in accordance with the present invention; that is, the N ECG signals are respectively minus $2^{K-1}$ and then divided by $2^{K-1}$ by the normalization device 210, so as to generate the N normalized signals x(n), where K is the bit number of the N ECG signals.

The discrete cosine transform device 220 is connected to the normalization device 210 for receiving the N normalized signals so as to perform a discrete cosine transform operation thereby generating N discrete cosine transform signals X[k]. The discrete cosine transform device 220 is a DCT-IV device, wherein the N discrete cosine transform signals X[k] can be expressed as:

$$X[k] = \sum_{n=0}^{N-1} x(n) \times \cos\left(\frac{(2n+1)(2k+1)\pi}{4N}\right), n = 0, 1, ..., N-1, \quad (1)$$

where x(n) represents the normalized signals.

The N discrete cosine transform signals X[k] are also known as DCT-IV coefficient, wherein k is an index for coefficient X[k]. In the present invention, N is 64, i.e., 64-point DCT-IV coefficients being calculated, X[0] is known as DC value, and X[1] X[63] are known as AC value.

Figure 5A:
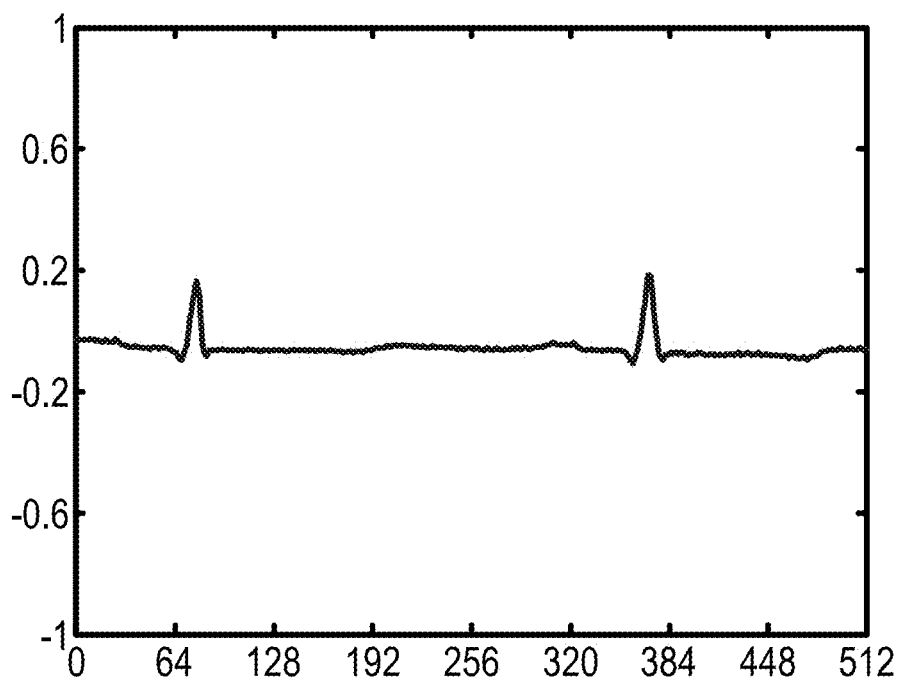
FIG. 5(A) schematically illustrates the ECG signals normalized to −1 to 1.
Figure 5B:
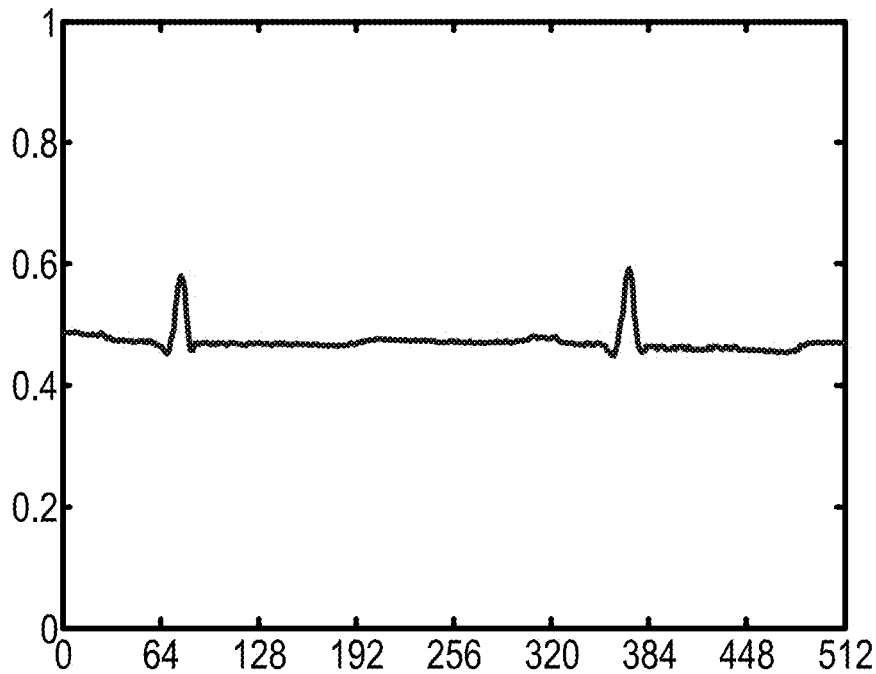
FIG. 5(B) schematically illustrates the ECG signals normalized to 0 to 1.
Figure 5C:
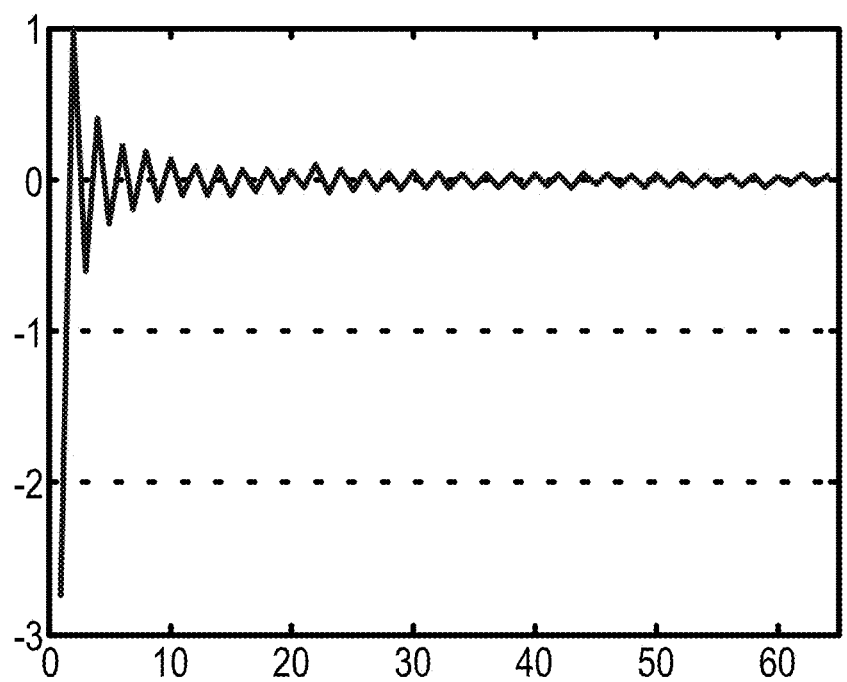
FIG. 5(C) schematically illustrates the ECG signals normalized to DCT-IV coefficient of −1 to 1.
Figure 5D:
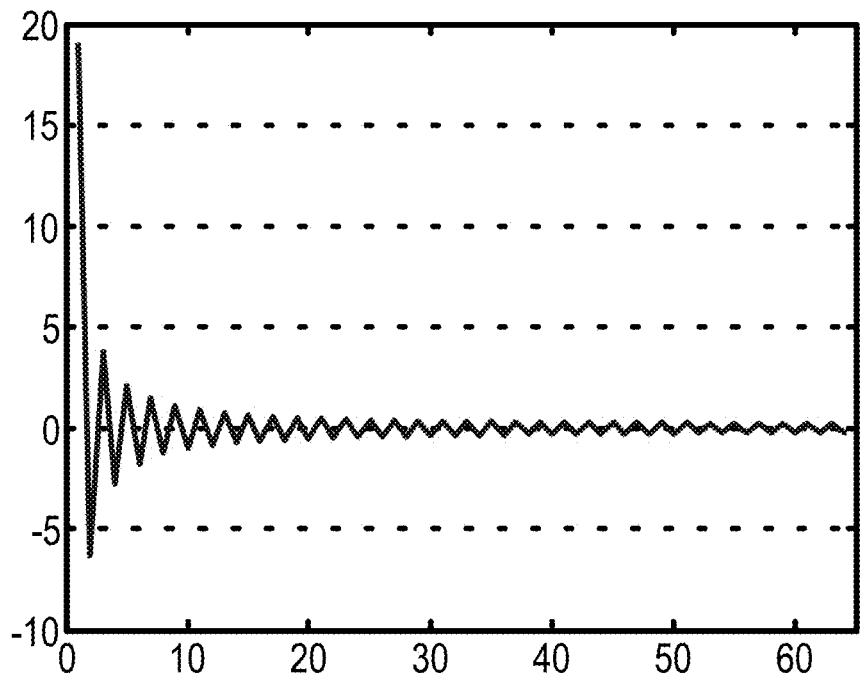
FIG. 5(D) schematically illustrates the ECG signals normalized to DCT-IV coefficient of 0 to 1.

Taking the front 512 samples of ECG signals in number-100 data of MIT-BIH database as an example, FIG. 5(A) schematically illustrates the ECG signals normalized to −1 to 1, FIG. 5(B) schematically illustrates the ECG signals normalized to 0 to 1, FIG. 5(C) schematically illustrates the ECG signals normalized to DCT-IV coefficient of −1 to 1, and FIG. 5(D) schematically illustrates the ECG signals normalized to DCT-IV coefficient of 0 to 1.

From the dynamic ranges of FIG. 5(C) and FIG. 5(D), it is observed that the dynamic range normalized to −1 to 1 is smaller than the dynamic range normalized to 0 to 1. The coefficient of small dynamic range has the advantage in that, after subsequent spectrum transformation and quantization step, the quantization values have small difference and are concentrated, so as to have better compression effect. Therefore, the present invention adopts the normalization of −1 to 1.

Figure 1:
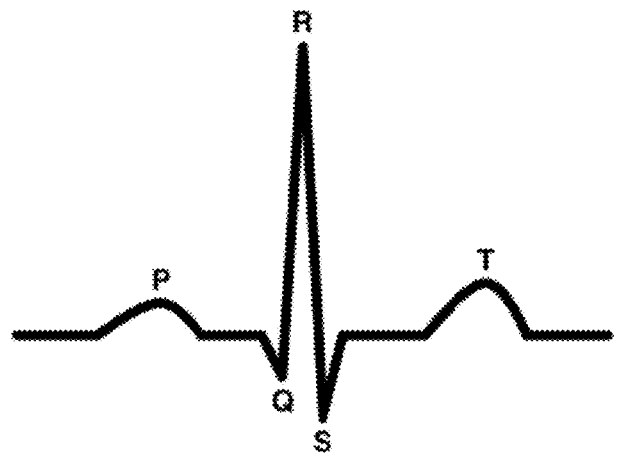
FIG. 1 is a schematic diagram illustrating the ECG signals.

From FIG. 5(C) and FIG. 5(D), it is observed that, after signals are transformed by DCT-IV, the value of DCT-IV coefficient is alternative between positive one and negative one. As shown in FIG. 1, ECG is composed of PQRST waveforms, and the above unique phenomenon usually occurs when the ECG is not QRS-complex waveform, due to that, when the input waveform is not QRS waveform, the magnitudes of signals are very close but violently swung (high frequency). Therefore, in order to explore and explain this phenomenon, it is assumed that the input signal is a constant value 1 which is applied into DCT-IV mathematics model, i.e., x(n)=1 being applied into equation (1), we have:

$$X[k] = \sum_{n=0}^{N-1} \cos\left(\frac{(2n+1)(2k+1)\pi}{4N}\right), k = 0, 1, ..., N-1. \quad (2)$$

Equation (2) is equivalent to summing up $$\cos\left(\frac{(2n+1)(2k+1)\pi}{4N}\right).$$

Figures 6, 7:
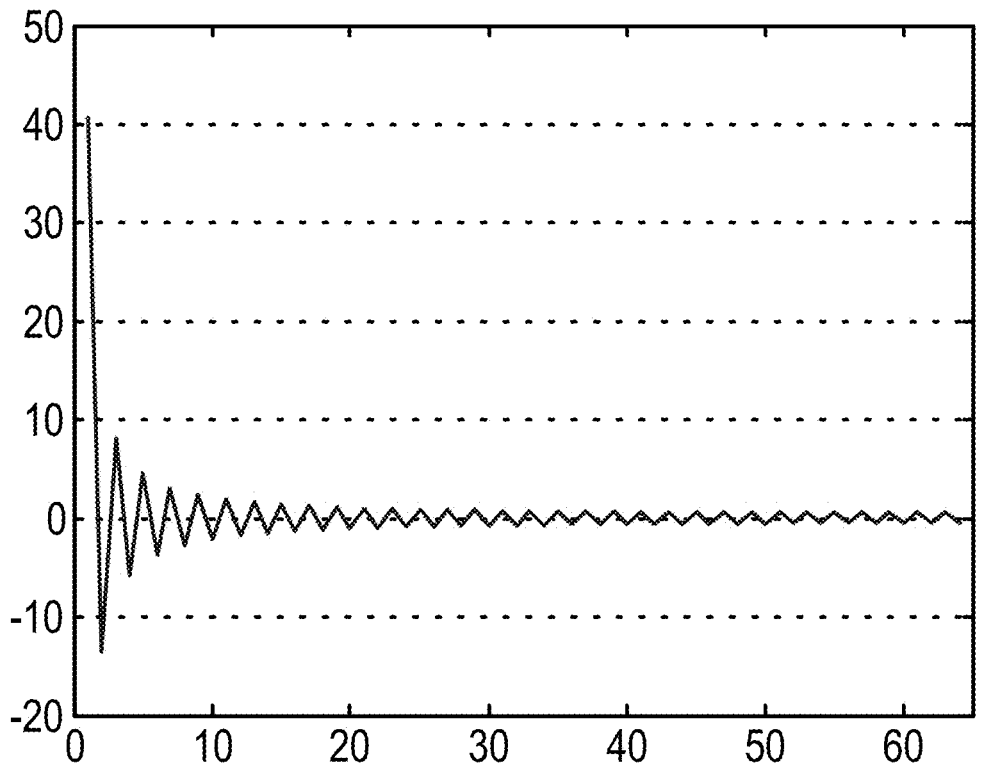
FIG. 6 schematically illustrates the calculation result of applying input constant value 1 and N=64 into DCT-IV mathematics model.
FIG. 7 shows the pseudo code for applying input constant value 1 and N=64 into DCT-IV mathematics model.

The result of summing up $$\cos\left(\frac{(2n+1)(2k+1)\pi}{4N}\right)$$

is shown in FIG. 6. FIG. 6 schematically illustrates the calculation result of applying input constant value 1 and N=64 into DCT-IV mathematics model, which has the same feature of alternative positive and negative value as that in FIG. 5(C) and FIG. 5(D). This physical feature means that, when there is non-QRS-complex waveform occurred, signals will slightly and frequently swing. After signals are multiplied by the cosine function $$\cos\left(\frac{(2n+1)(2k+1)\pi}{4N}\right)$$

in DCT-IV mathematics model and summed up, the cosine function $$\cos\left(\frac{(2n+1)(2k+1)\pi}{4N}\right)$$

causes the phenomenon of having positive and negative signs alternatively occurred and this regularity helps in increasing the compression ratio. FIG. 7 shows the pseudo code for applying input constant value 1 and N=64 into DCT-IV mathematics model.

The absolute value and quantization device 230 is connected to the discrete cosine transform device 220 for receiving the N discrete cosine signals X[k] to execute absolute value and quantization operation, so as to generate N quantization amplitude signals. The absolute value and quantization device 230 has a first quantization step, denoted as step1, and a second quantization step, denoted as step2, for performing absolute value operations to the N discrete cosine signals to generate N absolute-value discrete cosine signal coefficients, and then performs quantization operations to N absolute-value discrete cosine signal coefficients based on the first quantization step and the second quantization step, so as to generate the N quantization amplitude signals.

The sign and difference device 260 records the sign of the DCT-IV coefficient, and the absolute value and quantization device 230 takes the absolute value of the coefficient. By observing the characteristics of spectrum, FIG. 8) is obtained.

Figure 8A:
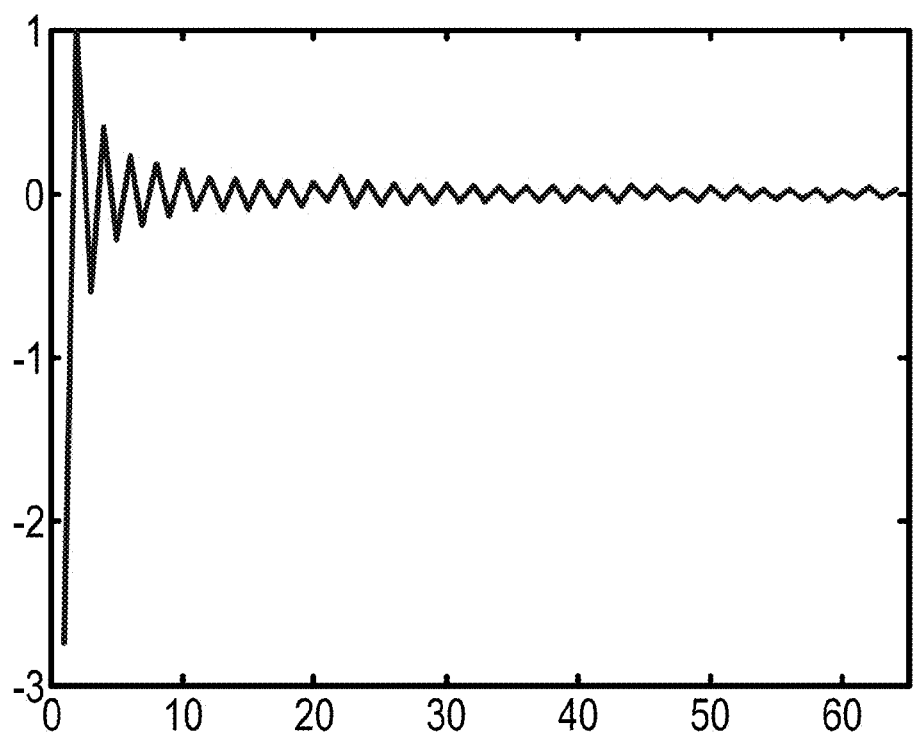
FIG. 8(A) and FIG. 8(B) respectively illustrate the N discrete cosine signals X[k] and the spectrum thereof in accordance with the present invention.
Figure 8B:
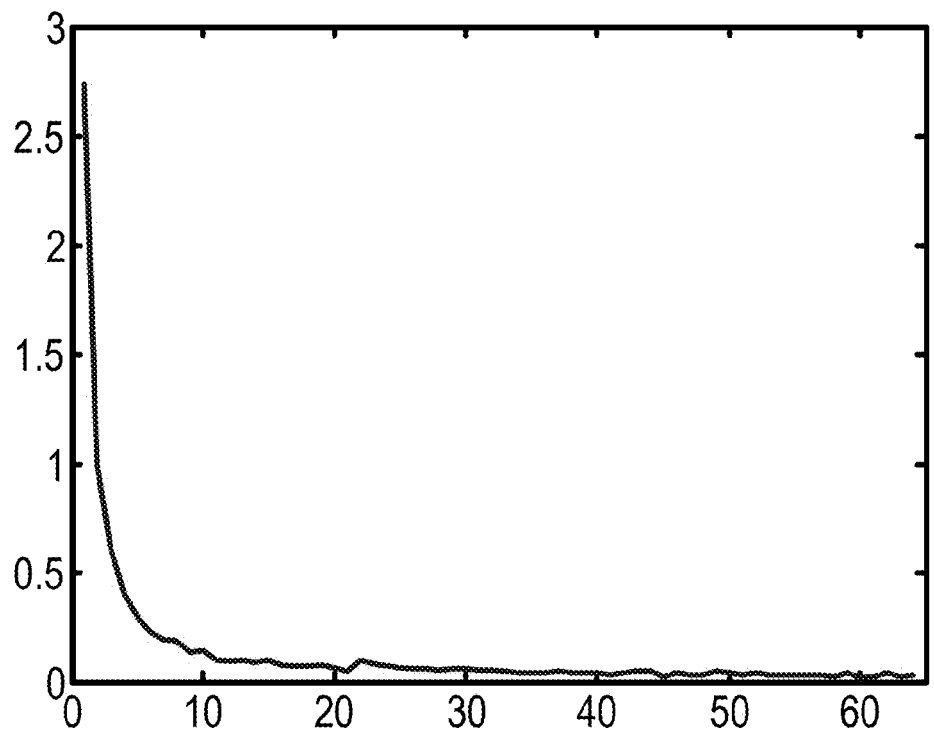

FIG. 8(A) and FIG. 8(B) respectively illustrate the N discrete cosine signals X[k] and the spectrum thereof, i.e., DCT-IV coefficients and DCT_IV spectrum. From FIG. 8(B), it can be seen that, after taking absolute value of the coefficient, the spectrum energy of ECG is concentrated on low frequency while energy level of middle/high frequency is relatively low. In order to achieve low distortion rate, the subsequent quantization strategy adopts non-uniform quantization scheme, in which the quantization interval (Step) for middle/low frequency is relatively large and the first quantization step "step1" is adopted, and the quantization interval (Step) for high frequency is relatively small and the second quantization step "step2" is adopted.

Figure 9A:
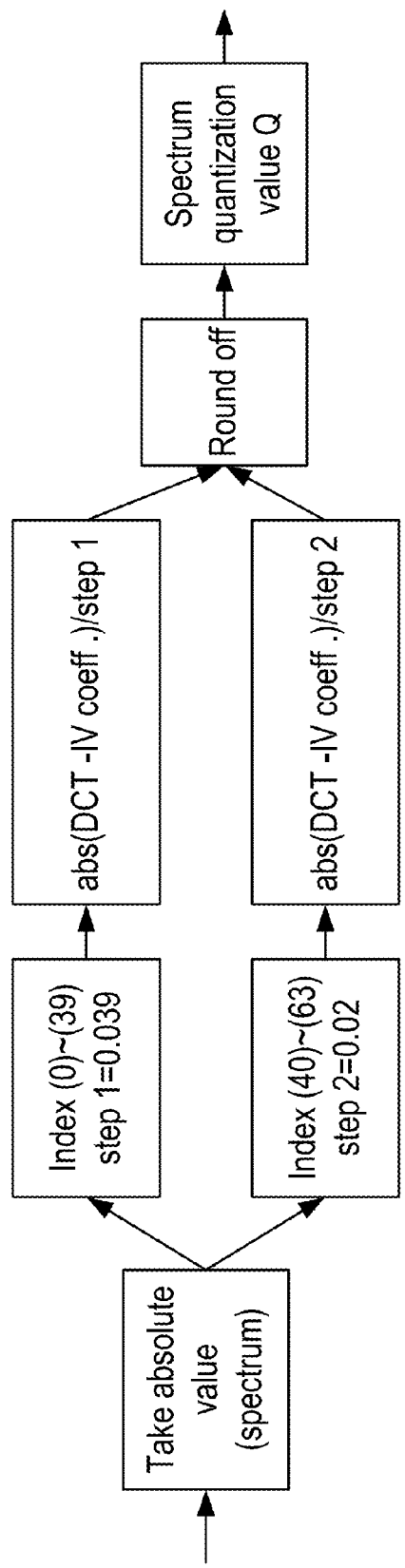
FIG. 9(A), FIG. 9(B) and FIG. 9(C) schematically illustrate the operation of the absolute value and quantization device.
Figure 9B:
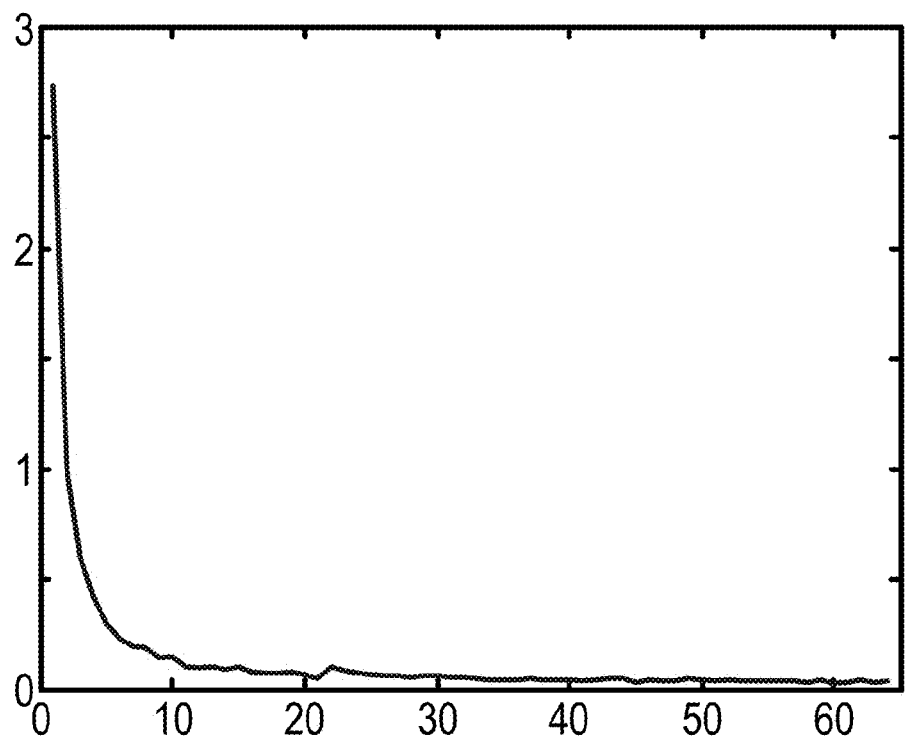
Figure 9C:
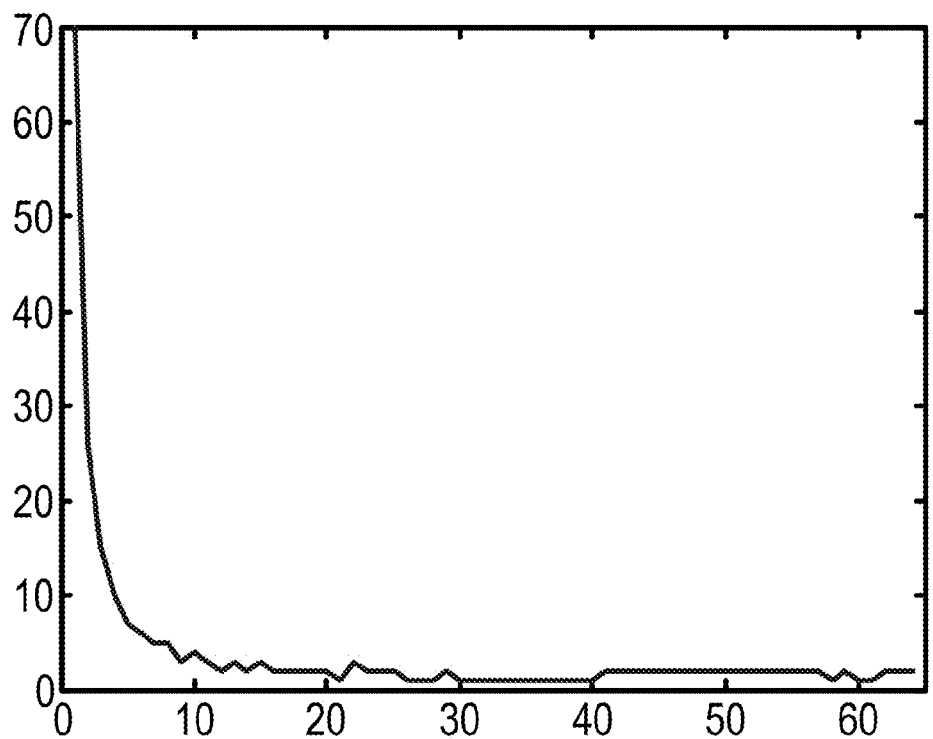
Figure 10:
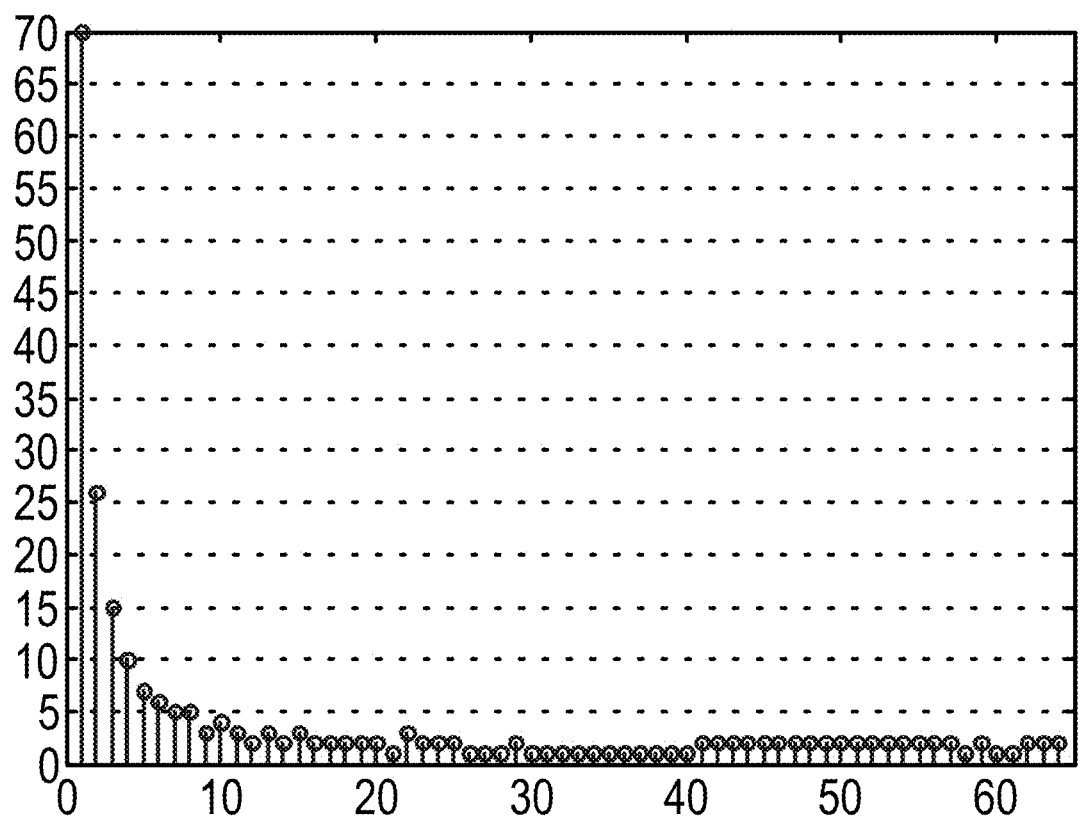
FIG. 10 schematically illustrates the DCT-IV spectrum quantization value Q in accordance with the present invention.

Based on the DCT-IV spectrums of 48 sets of arrhythmic ECG signals in MIT_BIH database, the value domain for the 48 sets of DCT-IV spectrums is in the range of 0 to 40. Due to considering on the characteristics of spectrum, the present invention adopts non-uniform quantization. When DCT-IV spectrum index value is (0)-(39), it uses 10 bits to record spectrum quantization value Q and uses the first quantization step "step1" to be 0.039, i.e., Q=10 bit, step1=0.039. When DCT-IV spectrum index value is (40)-(63), it uses 11 bits to record spectrum quantization value Q and uses the second quantization step "step2" to be 0.02, i.e., Q=11 bit, step2=0.02. FIG. 9(A), FIG. 9(B) and FIG. 9(C) schematically illustrate the operation of the absolute value and quantization device 230, in which the DCT-IV spectrum value is divided by the quantization step (step1, step 2) and then the closet integer value is taken, so as to determine the spectrum quantization value Q by rounding up or down. FIG. 10 schematically illustrates the DCT-IV spectrum quantization value Q in accordance with the present invention.

The difference coding device 240 is connected to the absolute value and quantization device 230 for receiving the N quantization amplitude signals, so as to perform a differential pulse code modulation (DPCM) operation to the N quantization amplitude signals thereby generating N difference signals.

Figure 11A:
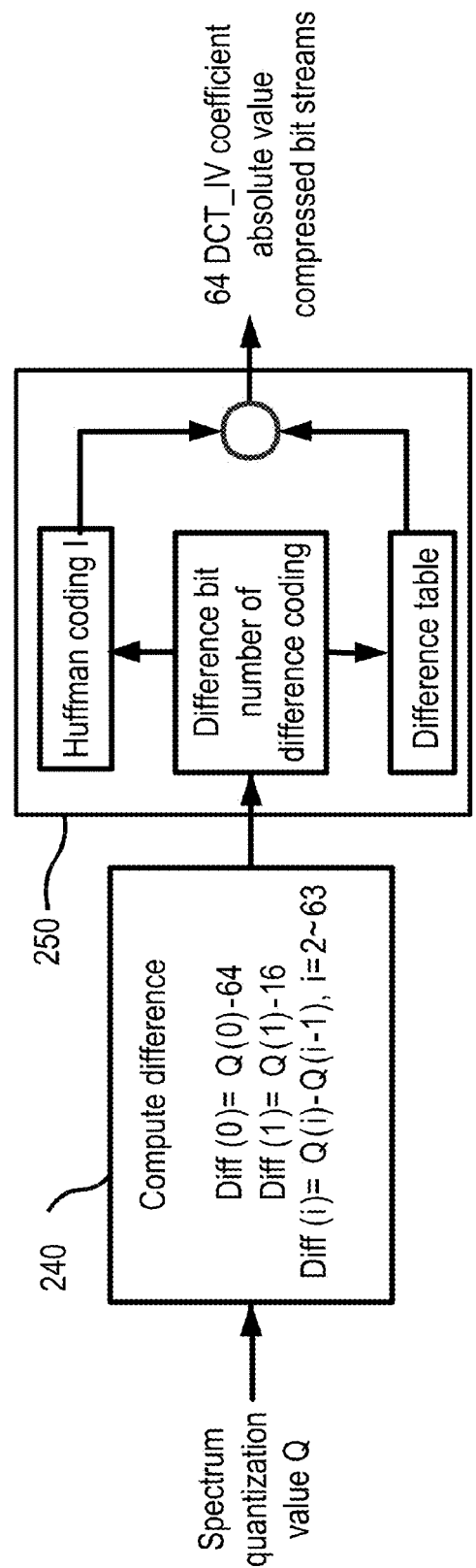
FIG. 11(A) and FIG. 11(B) schematically illustrate the operation of the difference coding device 240 in accordance with the present invention.
Figure 11B:
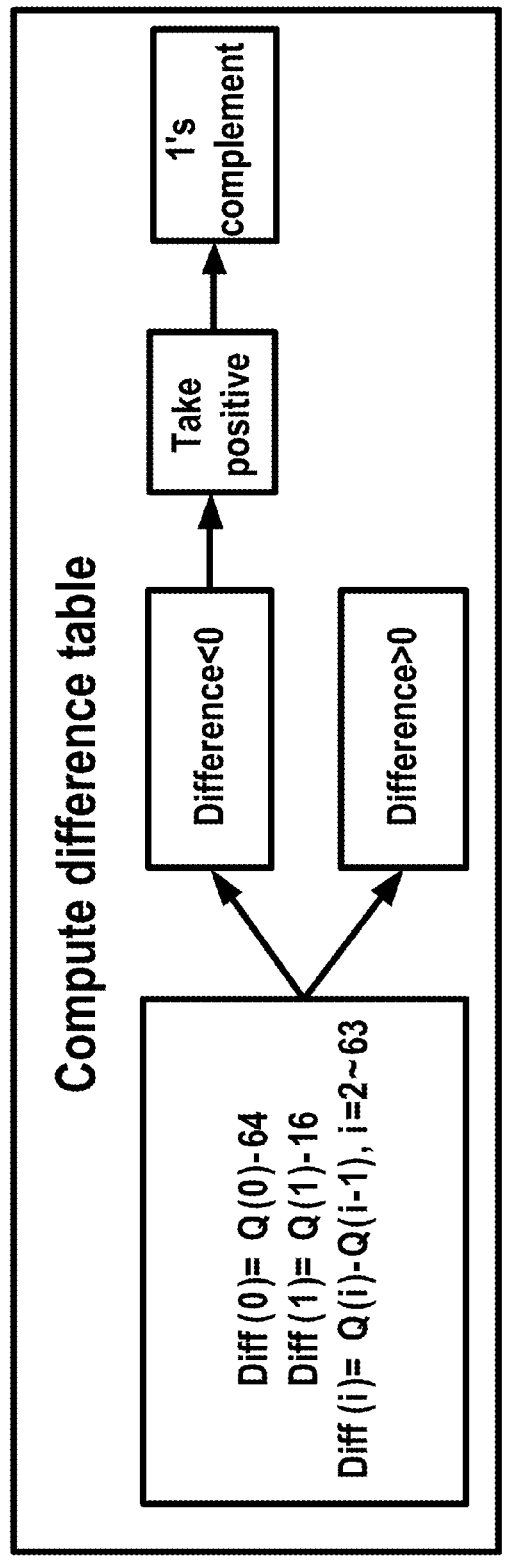

After quantizing the DCT-IV spectrum values in non-uniform manner, the DCT-IV spectrum quantization values Q in FIG. 10 are observed. Because the adjacent Q values are very close, it is suitable to use difference coding for compression. Such a method is a lossless compression and allows the compression ratio to increase. The method for recording the difference between the current quantization value and the previous quantization value is known as differential pulse code modulation (DPCM), i.e. Diff(i)=Q(i)−Q(i−1). However, as the difference between several Q values in front is relatively large, it may require more bits by using the method of taking difference between adjacent values. Therefore, the front two data are minus a fixed value (64, 16). FIG. 11(A) and FIG. 11(B) schematically illustrate the operation of the difference coding device 240. As shown, we have:

$$Diff(0)=Q(0)-64,$$

$$Diff(1)=Q(1)-16,$$

$$Diff(i)=Q(i)-Q(i-1), i=2 \text{ to } 63. \quad (3)$$

Figure 12A:
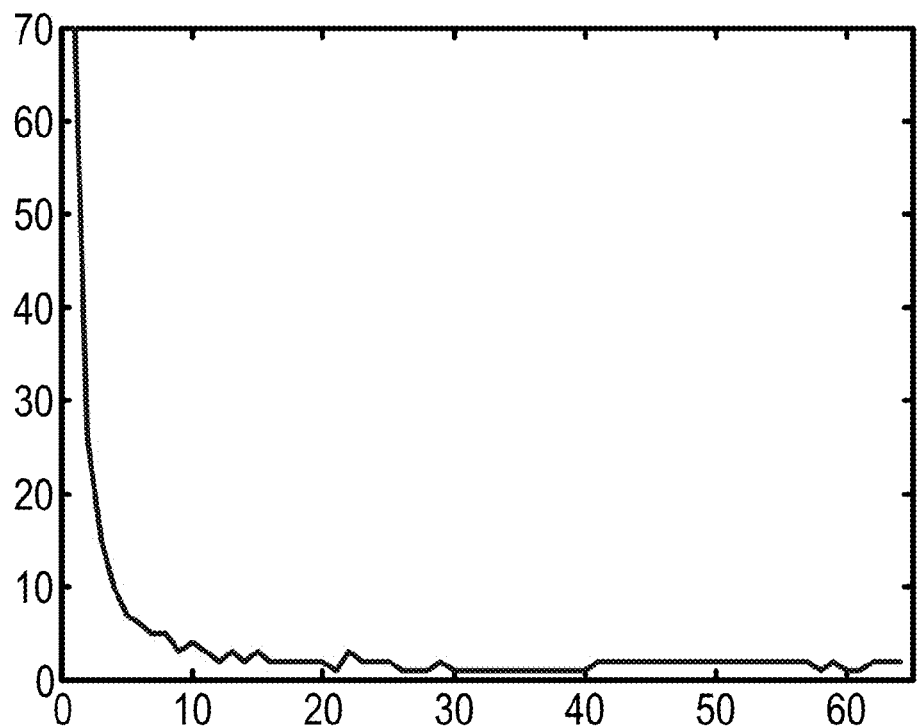
FIG. 12(A) and FIG. 12(B) schematically illustrate the DCT-IV spectrum quantization value Q and the difference Diff of quantization values of the present invention, respectively.
Figure 12B:
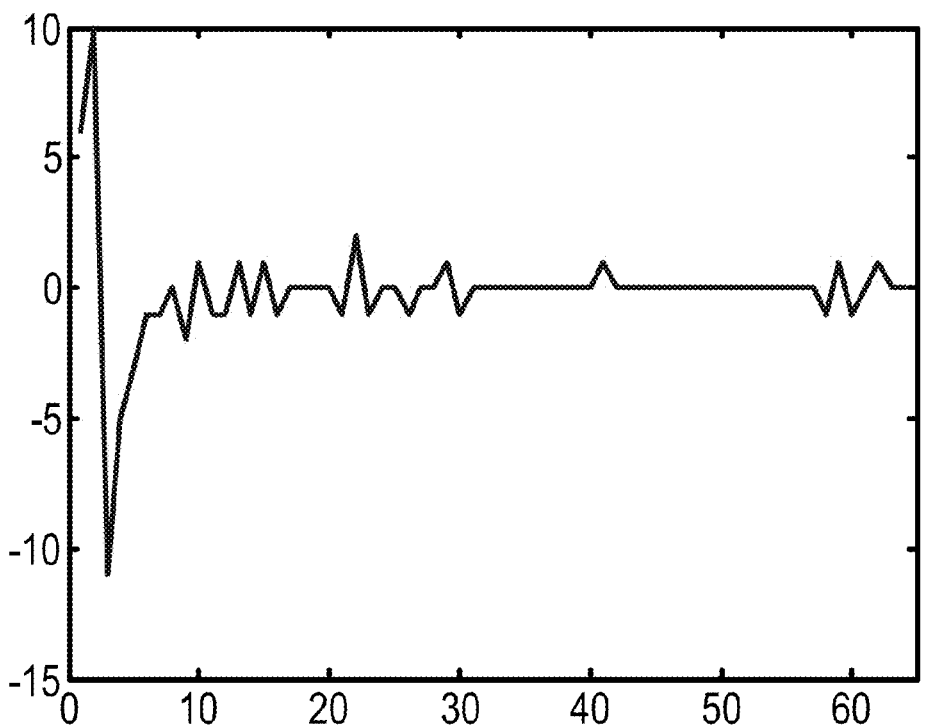

FIG. 12(A) and FIG. 12(B) schematically illustrate the DCT-IV spectrum quantization value Q and the difference Diff of quantization values of the present invention, respectively, in which the number of bits can be effectively saved by using difference. By taking FIG. 12(B) as an example, the use of difference coding in FIG. 12(B) results in a covered range of −10 to 10, which is much smaller than the covered range of 0 to 70 of the quantization value in FIG. 12(A). Therefore, the use of difference Diff to substitute the original quantization value Q can effectively reduce the number of bits required.

The first variable length coding device 250 is connected to the difference coding device 240 for performing variable length coding operation to the N difference signals so as to generate a first data stream, wherein the first variable length coding device 250 performs Huffman coding to the N difference signals to generate the first data stream.

FIG. 13 shows a difference table in accordance with the present invention. FIG. 14 shows a Huffman code table in accordance with the present invention. After determining the difference Diff, the first variable length coding device 250 depends on whether it is larger than 0 or smaller than 0, to calculate the address and difference bit number corresponding to the difference Diff in the difference table of FIG. 13 and then to find out the Huffman code corresponding to the difference bit number in the Huffman code table.

Taking the front four spectrum quantization values Q(0)= 70, Q(1)=26, Q(2)=15 and Q(3)=10 in FIG. 12(A) as an example, the differences can be represented as: Diff(0)=Q (0)−64, Diff(1)=Q(1)−16, Diff(2)=Q(2)−Q(1), and Diff(3)= Q(3)−Q(2), and thus Diff(0)=6, Diff(1)=10, Diff(2)=−11, and Diff(3)=−5. Then, the corresponding fields and addresses in the difference table of FIG. 13 are calculated as follows:

Diff(0)=6=110(binary), difference bit number=3, address=110;

Diff(1)=10=1010(binary), difference bit number=4, address=1010;

Diff(2)=−11 inversed to 11=1011(binary) which becomes 0100 by taking 1's complement, difference bit number=4, address=0100;

Diff(3)=−5 inversed to 5=101(binary) which becomes 010 by taking 1's complement, difference bit number=3, address=010.

Finally, the difference bit numbers are mapped to the Huffman codes in FIG. 14 as follows:

Diff(0), difference bit number=3, Huffman code=01000;

Diff(1), difference bit number=2, Huffman code=011;

Diff(2), difference bit number=4, Huffman code=01010;

Diff(3), difference bit number=3, Huffman code=01000.

The first variable length coding device 250 uses Huffman code+difference table address as the first data stream for output as follows:

01000 110 (1st), 011 10 (2nd), 01010 0100 (3rd), 01000 010 (4th), . . . .

FIG. 15 schematically illustrates the total bit number of difference coding in accordance with the present invention. From FIG. 15, it is known that the possibility of difference being 0 is 43.28%, indicating that 43.28% of data can be compressed to 1 bit. Similarly, the possibility of difference being 1 is 32.03%, indicating that 32.03% of data can be compressed to 3 bits. Therefore, about 75% of data can be compressed to less than 3 bits.

The sign and difference device 260 is connected to the discrete cosine transform device 220 for receiving the N discrete cosine signals to record the signs and differences of the N discrete cosine signals, so as to generate three sign signals (FIRST, SECOND and THIRD), wherein the sign and difference device 260 modifies part of the signs of the N discrete cosine signals so as to generate three modified sign signals Diff_FIRST, Diff_SECOND and Diff_THIRD.

The characteristics of the aforementioned DCT-IV coefficient can be applied in compression with the use of unique sign regularity of ECG DCT-IV coefficient. Because DCT-IV coefficient is alternative between positive sign and negative sign, simplification can be used to only record part of the signs so as to achieve the effect of compression, without having to record all 64 signs. In the present invention, there are only 33 signs recorded, which have index values of (0)-(31) and index value of (63). Such a method can increase the compression ratio up to about 13.04%. These 33 data are further compressed. The sign and difference device 260 divides the 33 signs into three parts, each having 11 signs, which are denoted as FIRST, SECOND and THIRD. Subsequently, difference operation and Huffman coding are performed to further increase the compression efficiency, and the compression ratio can be further increased by about 5.76%.

FIRST represents sign data string with DCT-IV coefficient index value of 0-10, SECOND represents sign data string with index value of 11-21, and THIRD represents sign data string with index value of 63 and index value of 22-31, wherein the most significant bit of THIRD is the sign of the discrete cosine signal (X[63]) with index value of 63. However, in most cases, the phenomenon of having alternative positive sign and negative sign occurs as shown in FIG. 5(C), in which the sign of X[0] is 1, the sign of X[1] is 0, the sign of X[2] is 1, . . . , the sign of X[63] is 0, where 0 represents positive and 1 represents negative.

Therefore, the sign and difference device 260 subtracts a fixed value from or adds a fixed value to FIRST, SECOND and THIRD, described in the following.

In most cases, FIRST is −683, SECOND is 682 and THIRD is 682, expressed as follows:

FIRST=101010101012=−683, 0:positive, 1:negative;

SECOND=010101010102=682;

THIRD=010101010102=682.　　　(3)

Therefore, we have:

FIRST+683=Diff_FIRST;

SECOND−682=Diff_SECOND;

THIRD−682=Diff_THIRD.　　　(4)

Figure 16A:
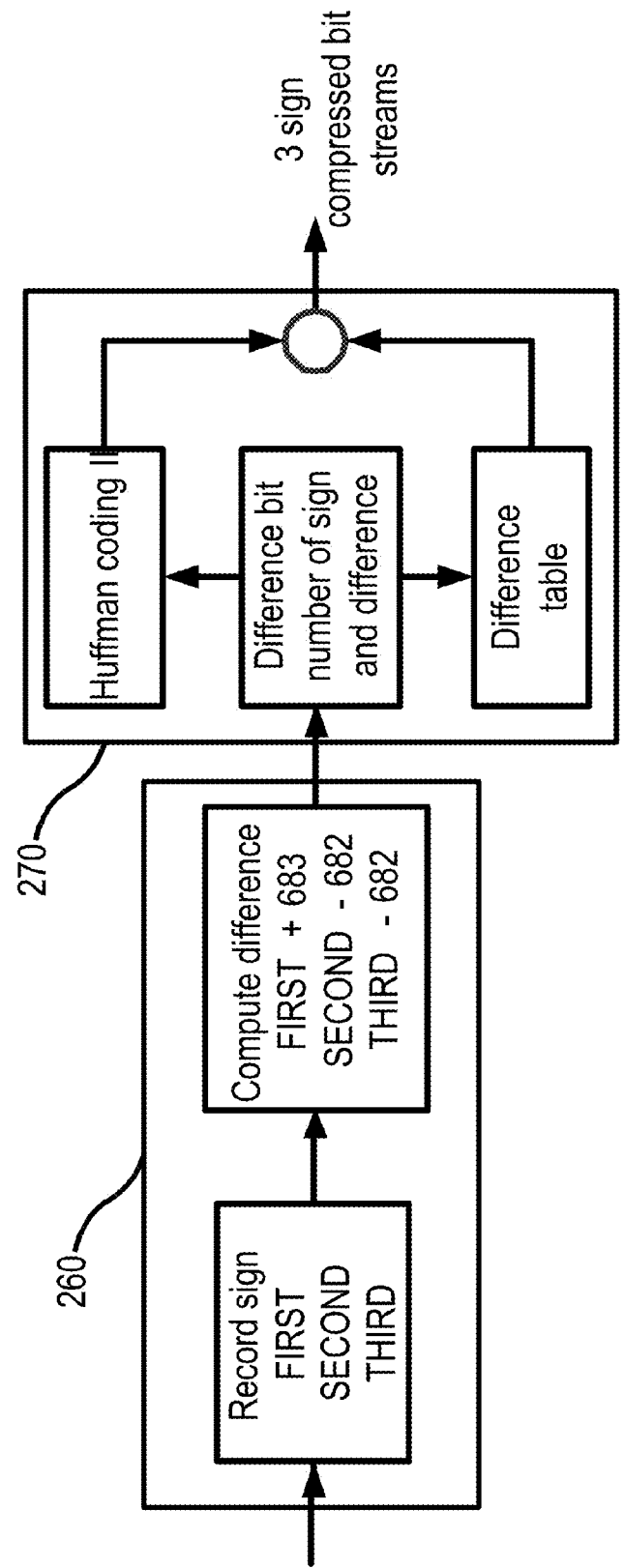
FIG. 16(A) and FIG. 16(B) schematically illustrate the operation of the sign and difference device in accordance with the present invention.
Figure 16B:
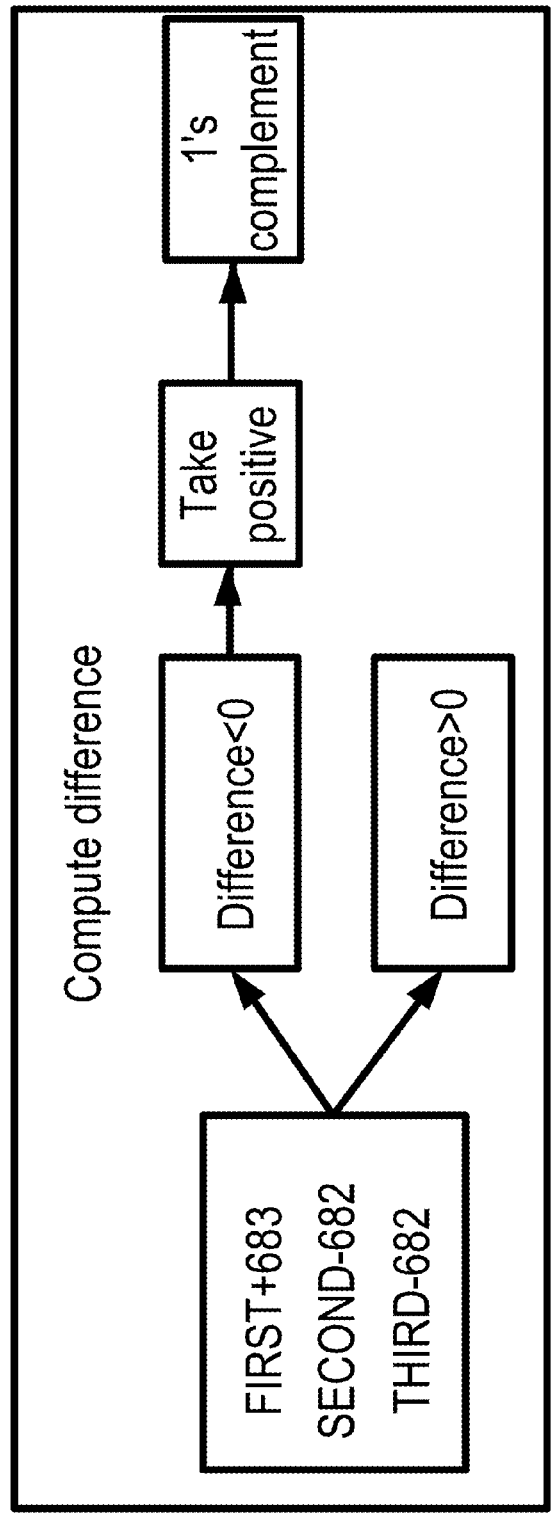

With a simple addition, the values of FIRST, SECOND and THIRD are controlled in a smaller dynamic range. FIG. 16(A) and FIG. 16(B) schematically illustrate the operation of the sign and difference device 260 in accordance with the present invention; i.e., for difference values Diff_FIRST, Diff_SECOND and Diff_THIRD, it calculates the difference table address and difference bit number based on whether the difference is larger than 0 or smaller than 0. As shown in FIG. 16(B), if the difference is larger than 0, the difference is the difference table address and the number of bits for representing the address is the difference bit number; if the difference is smaller than 0, the value has to be inversed to a positive one and then 1's complement thereof is taken to thus obtain a value equal to the difference table address, and the number of bits for representing the address is the difference bit number.

The second variable length coding device 270 is connected to the sign and difference device 260 for performing a variable length coding operation to the three sign and difference signals, so as to generate a second data stream, wherein the second variable length coding device 270 performs a Huffman coding to the three modified sign signals so as to generate the second data stream.

FIG. 17 shows another difference table in accordance with the present invention. FIG. 18 shows another Huffman code in accordance with the present invention. The second variable length coding device 270 is able to determine the table address and difference bit number form the difference, corresponding to the difference table as shown in FIG. 17. Next, the occurrence probability of difference bit number is used to generate the Huffman code as shown in FIG. 18. Then, the difference bit number is represented by Huffman code. Finally, the second variable length coding device 270 generates the second data stream based on the Huffman code+difference table address.

Taking the field of the difference table with the difference bit number being 3 as an example, the difference table address 000 corresponds to a value of −7, address 001 corresponds to a value of −6, and so on. As shown in FIG. 19, FIG. 19 schematically illustrates the difference table address for the difference bit number being 3.

In case of the difference being positive, taking Diff_FIRST=5 as an example, 5 is expressed as 101 in binary code and the bit number of 101 is 3. By looking up FIG. 17 and FIG. 19, it is known that the difference of 5 appears at the field with difference bit number being 3 and the address is 101. Then, the obtained difference bit number is encoded with the Huffman code table shown in FIG. 18, wherein difference bit number=3 corresponds to Huffman code of 1001110. Therefore, the final compressed bit stream is expressed as 1001110 101.

In case of the difference being negative, taking Diff_FIRST=−5 as an example, the negative difference value is first inversed to a positive one, and 5 is expressed as 101 in binary code. Then, the 1's complement of 101 is 010 and the bit number of 010 is 3. By looking up FIG. 17 and FIG. 19, it is known that the difference of −5 appears at the field with difference bit number being 3 and the address is 101. Then, the obtained difference bit number is encoded with the Huffman code table shown in FIG. 18. Therefore, the final compressed bit stream is expressed as 1001110 010.

Based on the occurrence probability of difference bit number 0-11, the Huffman code table, as shown in FIG. 18, is manufactured. The use of Huffman code to replace the difference bit number can increase the coding efficiency. After calculating the difference and analyzing the result, the probability of having 0 for the difference after addition/subtraction is over 50%. That is, each of FIRST, SECOND and THIRD requires 11 bits for recording. After taking difference, the number of times of having 0 for the results of FIRST, SECOND and THIRD is more than ½ of the total number of times. Then, after performing Huffman coding, the original 11-bit data is compressed to require only one bit for recording. FIG. 20 shows the bit number for sign compression flow in accordance with the present invention, wherein there is a probability of 56.8% to express 11-bit data by one bit, and there is a probability of 38% to use more bits than the original one, at most 15 bits, for expression. The use of difference and lossless Huffman can obtain effect in compression ratio. The recorded 33 DCT-IV coefficient signs are compressed to generate three compressed bit streams.

The mixer 280 is connected to the first variable length coding device 250 and the second variable length coding device 270 for mixing the first data stream and the second data stream, so as to generate a compressed ECG data stream. That is, after the compression flow, there are 67 compressed bit streams in total for output, wherein 3 of them are sign compressed bit streams and the remaining 64 of them are coefficient-converted compressed bit streams.

Figure 21:
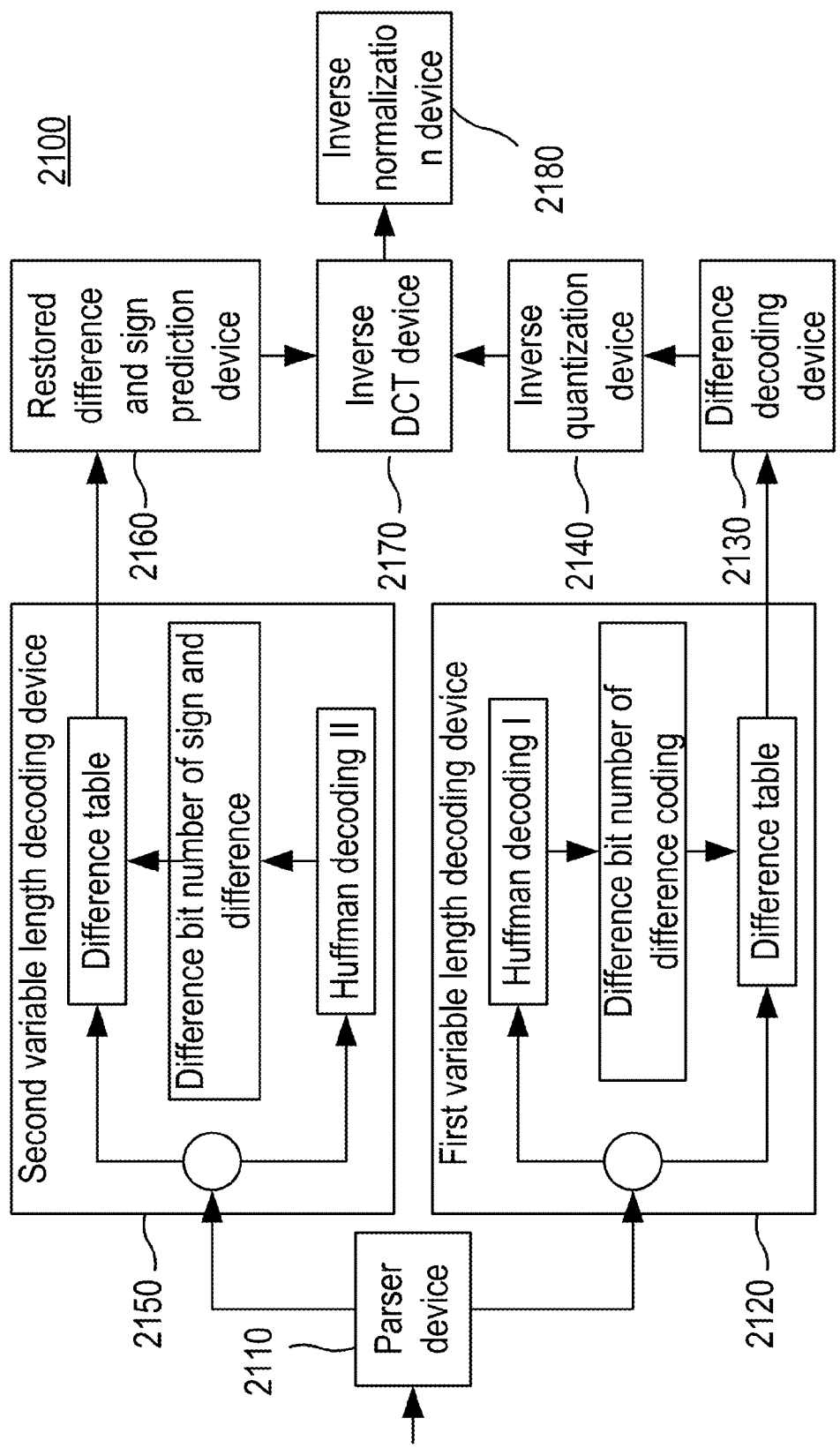
FIG. 21 is a block diagram of the ECG signal decompression system in accordance with a preferred embodiment of the present invention.

FIG. 21 is a block diagram of the ECG signal decompression system 2100 in accordance with a preferred embodiment of the present invention. The decompression system 2100 includes a parser device 2110, a first variable length decoding device 2120, a difference decoding device 2130, an inverse quantization device 2140, a second variable length decoding device 2150, a restored difference and sign prediction device 2160, an inverse discrete cosine transform device 2170, and an inverse normalization device 2180.

The decompression system can be divided into three parts. The first part relates to decompression of 3 sign compressed bit streams and decompression of the remaining 64 compressed bit streams. Then, the second part relates to how to restore the sign and DCT-IV coefficient. Finally, the third part performs inverse DCT-IV and inverse normalization to the restored DCT-IV coefficient, so as to obtain a reconstruction signal.

The parser device 2110 receives a compressed ECG data stream and analyzes the compressed ECG data stream, so as to generate a first data stream and a second data stream.

Figure 22:
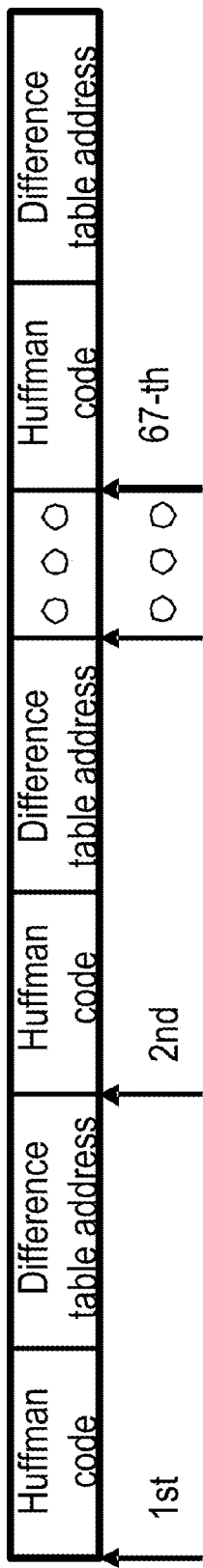
FIG. 22 schematically illustrates the compressed ECG data stream in accordance with the present invention.

FIG. 22 schematically illustrates the compressed ECG data stream in accordance with the present invention. When the decompression system 2100 receives 67 compressed bit streams each time, it uses the Huffman code table of FIG. 18 and the difference table of FIG. 17 to resolve the sign difference for the front 3 compressed bit streams (second data stream). For the remaining 64 compressed bit streams (first data stream), the Huffman code table of FIG. 14 and the difference table of FIG. 13 are used to resolve the quantization difference.

The first variable length decoding device 2120 is connected to the parser device 2110 for performing a variable length decoding operation to the first data stream so as to generate N difference signals, where N is a positive integer. The first variable length decoding device 2120 performs Huffman coding operation to the first data stream so as to generate N difference signals, where N is 64 in the present invention.

Because Huffman coding has the feature of uniqueness, when receiving a series of compressed stream, the decoding end first uses Huffman coding and the Huffman code table of FIG. 14 to find out the difference bit number and, at this moment, is aware of the number of bits occupied by the difference address following the Huffman code, thereby obtaining the difference via the difference table of FIG. 13.

Taking the decoding end receiving a sign compressed bit stream 01000 010xxx . . . as an example, by looking up the Huffman code table of FIG. 14, it can determine the difference bit number corresponding to the Huffman code 01000 to be 3, indicating that the next three bits (=010) following 01000 represent the difference table address. Therefore, from the difference table of FIG. 13, the filed with difference bit number=3 and difference table address=010, it can resolve a difference of −5.

Figure 23:
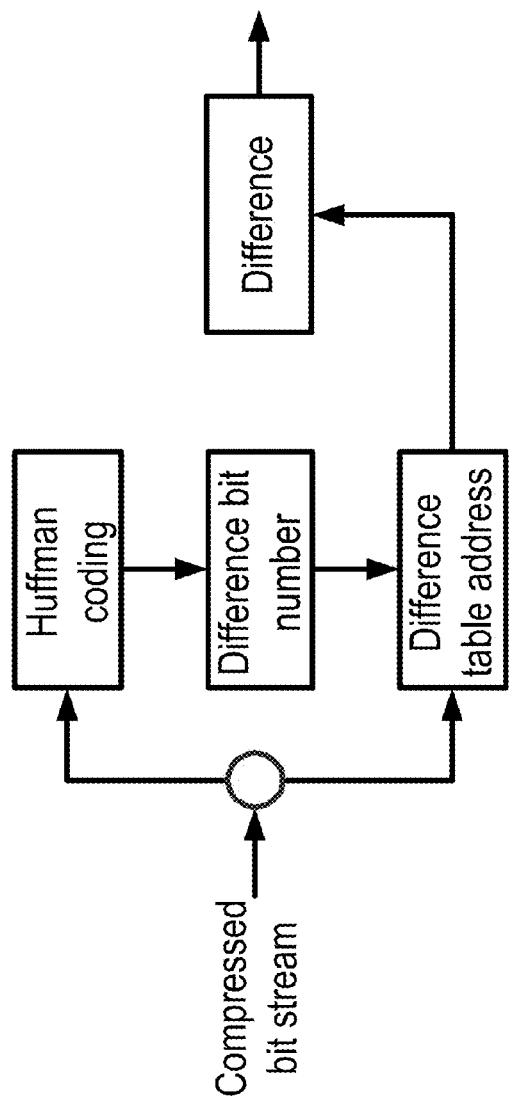
FIG. 23 schematically illustrates Huffman decompression in accordance with the present invention.

FIG. 23 schematically illustrates Huffman decompression in accordance with the present invention. No matter for the sign compressed bit stream or the compressed bit stream of DCT-IV transform coefficient, the decompression method is illustrated in FIG. 23. Both of them have the same difference table, but each of them has its own Huffman table. Further, after obtaining the differences, the methods for restoring sign and spectrum quantization value are slightly different.

The difference decoding device 2130 is connected to the first variable length decoding device 2120 for receiving the N difference signals and performing a differential pulse code modulation (DPCM) operation to the N difference signals, so as to generate 63 quantization amplitude signals.

Figure 24:
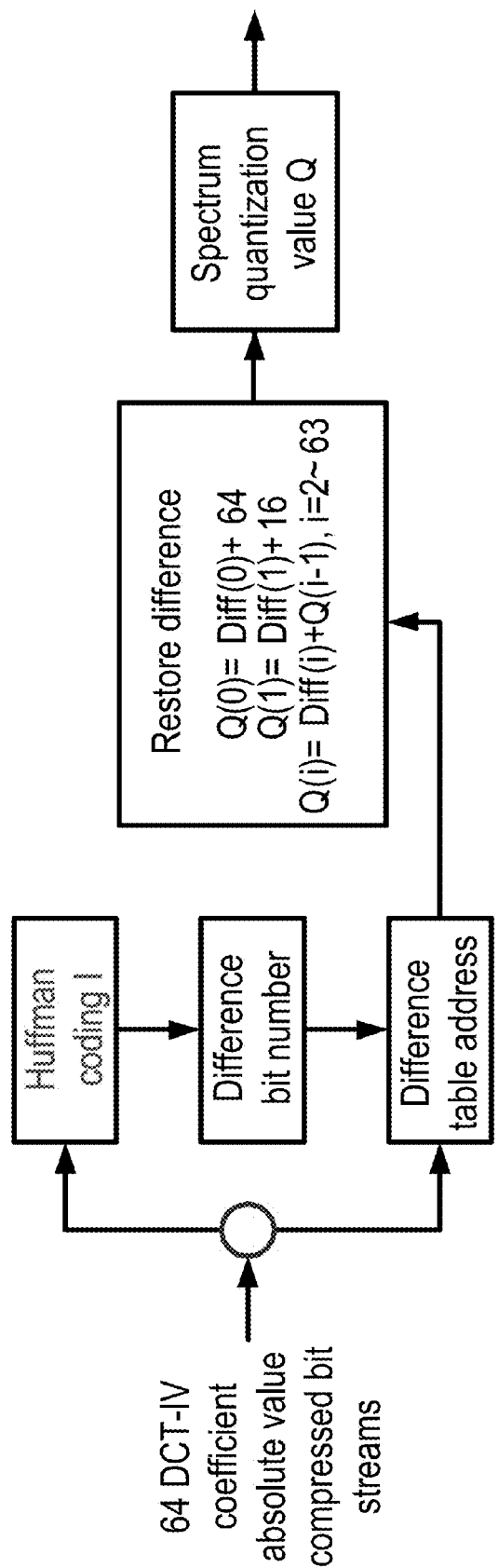
FIG. 24 schematically illustrates the operation of the difference decoding device in accordance with the present invention.

The decoding end receives the compressed bit stream of DCT-IV coefficient absolute value and decodes the corresponding differences, i.e., Diff(i), i=0-63. Then, similar to the aforementioned difference coding device 240, addition/subtraction and difference coding are used to restore the spectrum quantization values (or 64 quantization amplitude signals). FIG. 24 schematically illustrates the operation of the difference decoding device 2130 in accordance with the present invention. As shown, we have:

$$Q(0)=\text{Diff}(0)+64,$$

$$Q(1)=\text{Diff}(1)+16,$$

$$Q(i)=\text{Diff}(i)+Q(i-1), i=2-63. \quad (5)$$

The inverse quantization device 2140 is connected to the difference decoding device 2130 for receiving the N quantization amplitude signals and performing an inverse quantization operation, so as to generate inverse quantization signals of the N discrete cosine signals, wherein the inverse quantization device includes a first quantization step, denoted as step 1, and a second quantization step, denoted as step 2. The inverse quantization device performs an inverse quantization operation to the N quantization amplitude signals based on the first quantization step and the second quantization step, so as to generate inverse quantization signals of the N discrete cosine signals.

Figure 25:
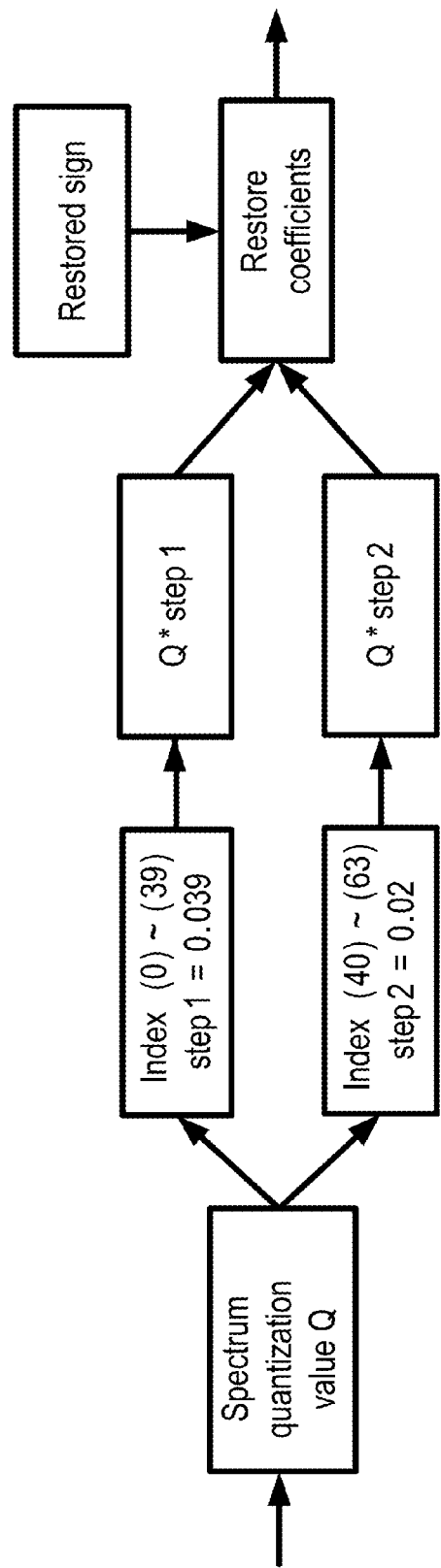
FIG. 25 schematically illustrates the operation of the inverse quantization device in accordance with the present invention.

FIG. 25 schematically illustrates the operation of the inverse quantization device 2140 in accordance with the present invention. The operation of inverse quantization is to multiply the spectrum quantization value Q with a quantization step (step1, step2) for restoring. However, the values after inverse quantization are all positive ones, but not the true DCT-IV coefficients. It is necessary to correspond the 64 signs restored and predicted by the second variable length decoding device 2150 and the restored difference and sign prediction device 2160 to each of the indexes, so as to obtain the restored DCT-IV coefficients.

The second variable length decoding device 2150 is connected to the parser device 2110 for performing a variable length decoding operation to the second data stream, so as to generate three sign and difference signals, wherein the second variable length decoding device 2150 performs a Huffman coding to the second data stream to generate the three modified sign signals.

Taking the decoding end receiving a sign compressed bit stream 1001110 010xxx . . . as an example, by looking up the Huffman table shown in FIG. 18, it is determined that the Huffman code 1001110 corresponds to a difference bit number=3, indicating that the next three bits (=010) following 1001110 represent a difference table address. Therefore, from the difference table of FIG. 17, the column of difference bit number=3 in FIG. 18, and difference table address=010 in FIG. 19, it is able to solve the difference=−5.

The restored difference and sign prediction device 2160 is connected to the second variable length decoding device 2150 for receiving difference signals of the three signs, so as to execute a restored difference and sign prediction operation thereby generating the signs of the N discrete cosine signals The restored difference and sign prediction device 2160 subtracts a first constant from the first modified sign signal, and adds a second constant to the second and third modified sign signals, so as to generate first to third temporal signals. The restored difference and sign prediction device 2160 performs sign prediction to the first to third temporal signals, so as to generate the signs of the N discrete cosine signals.

Figure 26:
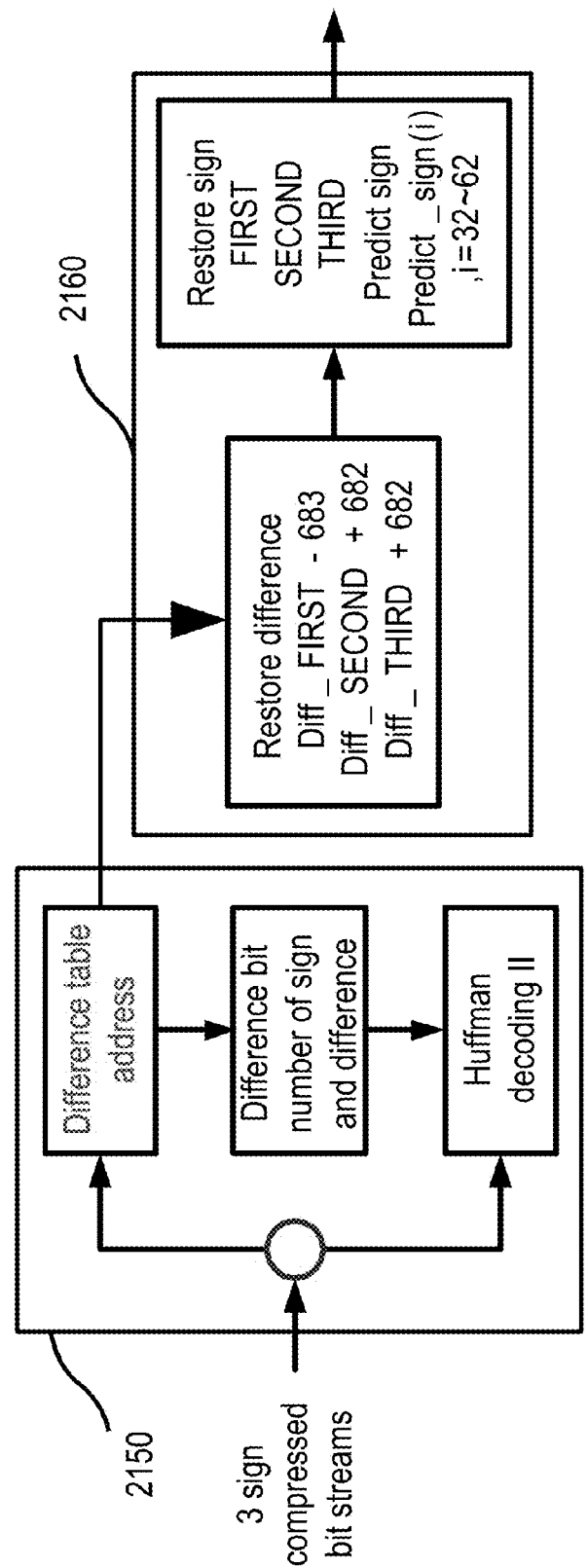
FIG. 26 schematically illustrates the operation of the restored difference and sign prediction device in accordance with the present invention.

FIG. 26 schematically illustrates the operation of the restored difference and sign prediction device 2160 in accordance with the present invention. The restored difference and sign prediction device 2160 receives the differences decoded from the sign compressed bit streams, i.e., Diff_FIRST, Diff_SECOND and Diff_THIRD. Then, as shown in FIG. 26, the restored difference and sign prediction device 2160 restores FIRST, SECOND and THIRD through addition and subtraction as follows:

FIRST=Diff_FIRST−683,

SECOND=Diff_SECOND+682,

THIRD=Diff_THIRD+682. (6)

After obtaining FIRST, SECOND and THIRD, the restored difference and sign prediction device 2160 restores 33 signs for DCT-IV coefficients X[0] to X[31] and X[63] of the original signal, while the remaining 31 signs are restored by prediction.

In the flow of compression, due to the alternation of positive sign and negative sign, only 33 signs are recorded. Therefore, in compression, the 32-th to 62-th signs are restored by prediction, which is based on the 63-th sign.

When X[63] is positive, i.e., sign(63)=0, X[62] is predicted to be negative, i.e., predict_sign(62)=1; X[61] is predicted to be positive, i.e., predict_sign(61)=0; similar prediction is applied until X[33] is positive, i.e., predict_sign(33)=0 and X[32] is negative, i.e., predict_sign(32)=1.

When X[63] is negative, i.e., sign(63)=1, X[62] is predicted to be positive, i.e., predict X[61] sign(62)=0; X[61] is predicted to be negative, i.e., predict_sign(61)=1; similar prediction is applied until X[33] is negative, i.e., predict_sign (33)=1 and X[32] is positive, i.e., predict_sign(32)=0. The flow of sign restoring is shown in FIG. 26.

The inverse discrete cosine transform device 2170 is connected to the inverse quantization device 2140 and the restored difference and sign prediction device 2160 for receiving the inverse quantization signals of the N discrete cosine signals and the signs of the N discrete cosine signals so as to generate the N discrete cosine signals X[k], and performing inverse discrete cosine operation to the N discrete cosine signals X[k] so as to generate N normalized signals X[n], wherein the inverse discrete cosine transform device 2170 is an type IV inverse discrete cosine transform (IDCT-IV) device.

Figure 27:
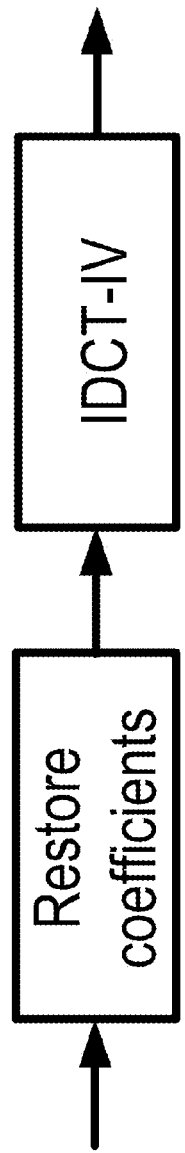
FIG. 27 schematically illustrates the operation of the inverse discrete cosine transform device.

After obtaining the restored DCT-IV coefficients, it then computes type IV inverse discrete cosine transformation, as shown in FIG. 27. FIG. 27 schematically illustrates the operation of the inverse discrete cosine transform device 2170. An IDCT-IV mathematics model of N points is defined as follows:

$$x(n) = \frac{2}{N}\sum_{k=0}^{N-1} X[k] \times \cos\left(\frac{(2k+1)(2n+1)\pi}{4N}\right), k = 0, 1, \ldots, N-1, \quad (7)$$

where X[n] represents N normalized signals and X[k] represents the N discrete cosine signals.

The inverse normalization device 2180 is connected to the inverse discrete cosine transform device 2170 for receiving N normalized signals and performing inverse normalization operation to the N normalized signals so as to generate N ECG signals.

Figure 28:
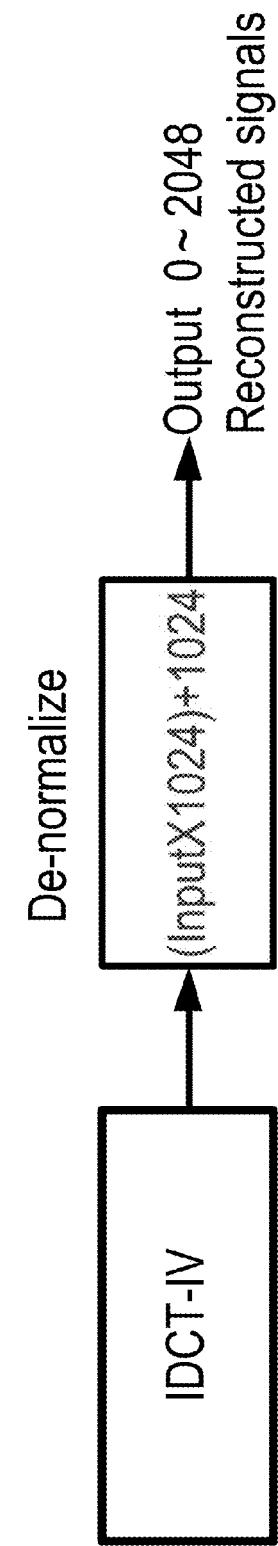
FIG. 28 schematically illustrates the operation of the inverse normalization device.

FIG. 28 schematically illustrates the operation of the inverse normalization device 2180, wherein the N normalized signals are respectively multiplied by $2^{K-1}$ and then added with $2^{K-1}$, so as to generate the N ECG signals, where K is the bit number of the N ECG signals.

In signal compression, some comparison indexes are provided as follows:

(1) Compression ratio:

$$CR = \frac{\text{Number of original data bits}}{\text{Number of compressed bits}}; \quad (8)$$

(2) Percent rms difference:

$$PRD(\%) = 100 \times \sqrt{\frac{\sum_{n=0}^{N-1}[X_s(n) - X_r(n)]^2}{\sum_{n=0}^{N-1}[X_s(n)]^2}}; \quad (9)$$

(3) Quality score:

$$QS = \frac{CR}{PRD}; \quad (10)$$

(4) Percent rms difference normalized:

$$PRDN(\%) = 100 \times \sqrt{\frac{\sum_{n=0}^{N-1}[X_s(n) - X_r(n)]^2}{\sum_{n=0}^{N-1}[X_s(n) - \overline{X}]^2}}; \quad (11)$$

(5) Root mean square:

$$RMS = \sqrt{\frac{\sum_{n=0}^{N-1}[X_s(n) - X_r(n)]^2}{N}}; \quad (12)$$

(6) Signal to noise ratio:

$$SNR = 10 \times \log\left(\frac{\sum_{n=0}^{N-1}[X_s(n) - \overline{X}]^2}{\sum_{n=0}^{N-1}[X_s(n) - X_r(n)]^2}\right); \quad (13)$$

wherein $X_s$ represents the original signal, $X_r$ represents the constructed signal, $\overline{X}$ represents the averaged original signal, and N is the total number of original signals.

The present invention performs analysis for three relatively important measurement indexes CR, PRD and QS as follows:

CR value is the compression ratio. According to expression (6), the numerator is in the original signal storage format that is 16-bit, and the denominator is the total bit number of the compressed signal, representative of the amount of data being compressed, a larger value indicating a smaller storage space.

PRD value is the power rate distortion representative of the degree of error between the constructed signal and the original, a lower value indicating a smaller distortion.

QS value represents the quality score, a higher score indicating a better compression efficiency. Because CR and PRD value will influence with each other, high CR value means high PRD value and low CR value means low PRD value. Therefore, since it is desired to have high CR value and low PRD value, the compression method of the compression must have a trade-off therebetween. QS value can directly reflect whether the compression method of a compression system is efficient or not. If the trade-off is excellent, the score is high.

Figure 29:
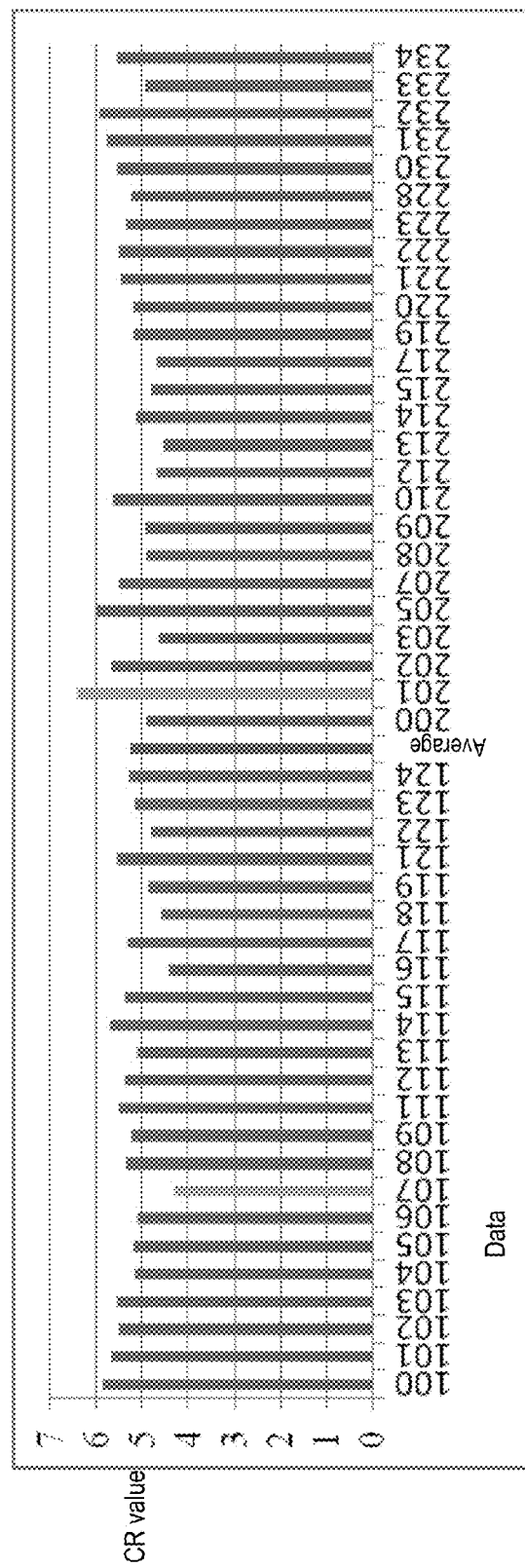
FIG. 29, FIG. 30 and FIG. 31 schematically illustrate the results of testing each set of database with the measurement indexes.
Figure 30:
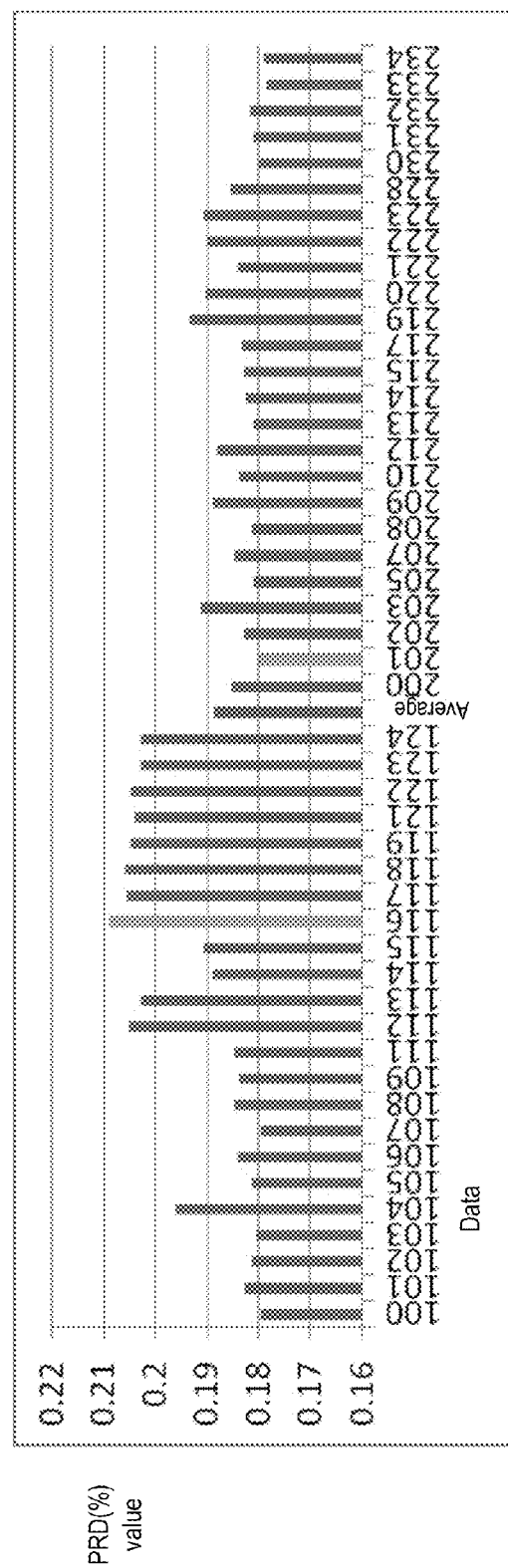
Figure 31:
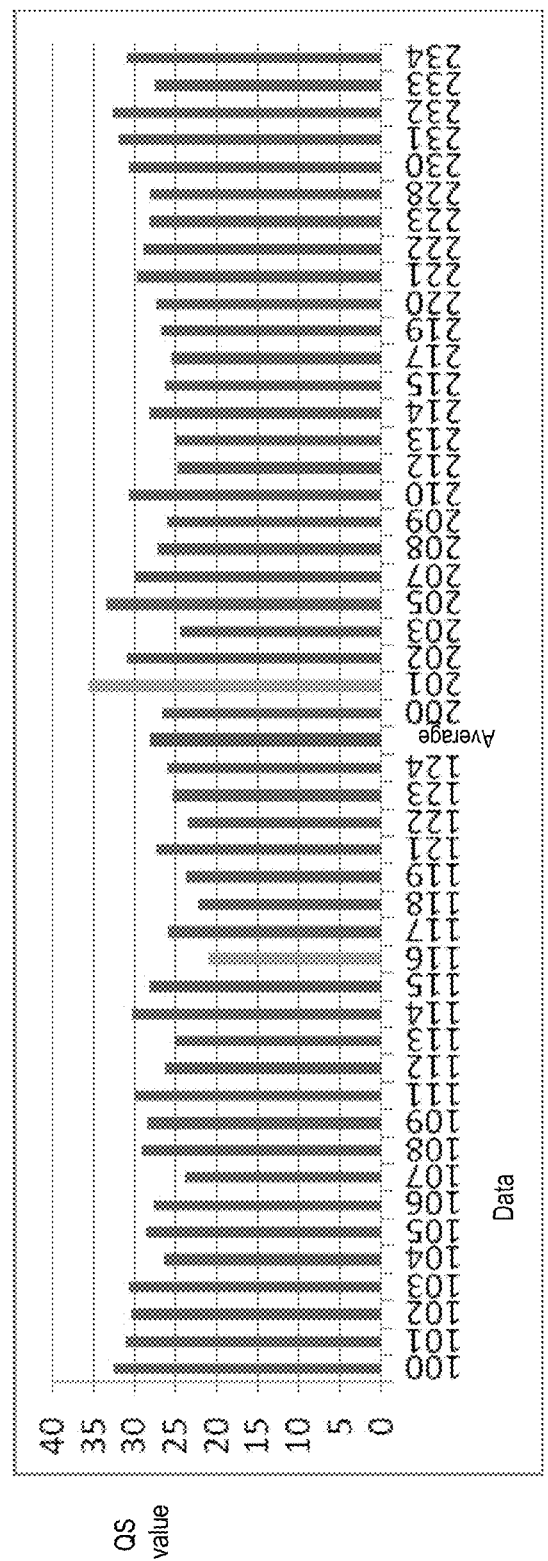

For each index of the compression method, 48 sets of MIT-BIH arrhythmia database files are used as test signals. The results of testing each set of database with the measurement indexes are respectively illustrated in FIG. 29, FIG. 30 and FIG. 31.

In the presentation of all data, the 201-st set has the best CR value 6.40, and the worst CR value 4.29 appears at the 107-th set. The 201-st set has best PRD value 0.18, and the worst PRD value 0.21 appears at the 116-th set. For the QS value, the 201-st set has the best QS value 35.60, and the worst QS value 21.07 appears at the 116-th set. The detailed measurement index data is shown in Table 1.

The compression system of the present invention has a window size 100% identical to that in article 1 (SangJoon Lee; Jungkuk Kim; Myoungho Lee "A Real-Time ECG Data Compression and Transmission Algorithm for an e-Health Device", Biomedical Engineering, IEEE Transactions on, vol. 58, no. 9, pp. 2448-2455, September 2011), which can conserve all DCT-IV coefficients and the input signal has a 16-bit storage format. The data is shown in Table 2. The present invention has a better CR value, a relatively lower PRD value, and a higher QS value, while the presentation of other indexes is also excellent.

Besides, in article 2 (Bendifallah, A.; Benzid, R.; Boulemden, M. "Improved ECG compression method using discrete cosine transform", Electronics Letters, vol. 47, no. 2, pp. 87-89, January 2011), and article 3 (Alam, M. S.; Rahim, N. M. S. "Compression of ECG signal based on its deviation from a reference signal using discrete cosine transform", Electrical and Computer Engineering 2008, International Conference, pp. 53-58, 20-22 Dec. 2008), the input uses 11-bit data format. For comparison, the original CR value is multiplied with 16/11 and asterisk (*) indicates the result that has been compressed to the same scale, Although articles 2 and 3 have better compression ratio, the relatively larger PRD value will cause low QS value and thus the overall compression efficiency is degraded by 3 to 4 times.

The present invention makes use of the sign relation of DCT-IV coefficients and the characteristics of spectrum quantization to represent each data by recording the difference while retaining all high-frequency information, and further uses Huffman coding to increase compression efficiency. Different from the prior conversion coding, the present invention selects to retain high-frequency component so as to effectively reduce the rate of distortion. Further, the spectrum quantization values of DCT-IV are close in high-frequency region, which can facilitate in increasing the compression ratio.

The ECG signal compression system and decompression system of the present invention use 48 sets of arrhythmia data in MIT-BIH database as test signals. The MIT-BIH database has a sampling rate of 360 Hz and an A/D converting resolution of 11 bits. Test results for all 48 sets are CR=5.2, PRD=0.19, QS=29.93. In comparison with articles 1, 2 and 3, the compression method of the present invention is excellent in terms of QS value. QS is a measurement index involving CR value and PRD value. A high QS value indicates that an algorithm has good trade-off between CR value and PRD value, i.e., the compression method of the present invention has excellent representation.

TABLE 1

| | | Measurement Index | | | | |
|---|---|---|---|---|---|---|
| Data | CR | PRD (%) | PRDN (%) | RMS | SNR | QS |
| 100 | 5.86 | 0.18 | 4.48 | 1.73 | 26.98 | 32.61 |
| 101 | 5.69 | 0.18 | 3.39 | 1.77 | 29.40 | 31.13 |
| 102 | 5052 | 0.18 | 4.64 | 1.77 | 26.67 | 30.44 |
| 103 | 5.55 | 0.18 | 2.75 | 1.77 | 31.23 | 30.76 |
| 104 | 5.16 | 0.20 | 3.84 | 1.92 | 28.32 | 26.35 |
| 105 | 5.18 | 0.18 | 2.20 | 1.78 | 33.16 | 28.57 |
| 106 | 5.10 | 0.18 | 2.48 | 1.83 | 32.11 | 27.67 |
| 107 | 4.29 | 0.18 | 1.04 | 1.78 | 39.67 | 23.87 |
| 108 | 5.37 | 0.18 | 3.01 | 1.81 | 30.44 | 29.08 |
| 109 | 5.22 | 0.18 | 1.81 | 1.81 | 34.85 | 28.40 |
| 111 | 5.53 | 0.18 | 3.57 | 1.83 | 28.95 | 29.91 |
| 112 | 5.37 | 0.20 | 3.94 | 1.76 | 28.08 | 26.21 |
| 113 | 5.09 | 0.20 | 2.45 | 2.02 | 32.22 | 25.12 |
| 114 | 5.70 | 0.19 | 5.48 | 1.88 | 25.23 | 30.16 |
| 115 | 5.38 | 0.19 | 2.44 | 1.77 | 32.27 | 28.26 |
| 116 | 4.40 | 0.21 | 1.33 | 1.77 | 37.50 | 21.07 |
| 117 | 5.31 | 0.21 | 3.68 | 1.76 | 28.69 | 25.83 |
| 118 | 4.57 | 0.21 | 2.06 | 1.76 | 33.72 | 22.20 |
| 119 | 4.86 | 0.20 | 1.64 | 1.76 | 35.69 | 23.74 |
| 121 | 5.55 | 0.20 | 2.92 | 1.76 | 30.68 | 27.23 |
| 122 | 4.80 | 0.20 | 2.40 | 1.76 | 32.39 | 23.45 |
| 123 | 5.15 | 0.20 | 3.02 | 1.76 | 30.39 | 25.93 |
| 124 | 5.27 | 0.20 | 1.90 | 1.76 | 34.40 | 25.99 |
| 200 | 4.91 | 0.19 | 2.45 | 1.86 | 32.21 | 26.51 |
| 201 | 6.40 | 0.18 | 4.60 | 1.79 | 26.74 | 35.61 |
| 202 | 5.67 | 0.18 | 3.05 | 1.82 | 30.31 | 30.99 |
| 203 | 4.65 | 0.19 | 1.92 | 1.90 | 34.34 | 24.37 |
| 205 | 6.04 | 0.18 | 4.43 | 1.74 | 27.07 | 33.39 |
| 207 | 5.52 | 0.18 | 2.59 | 1.83 | 31.75 | 29.90 |
| 208 | 4.91 | 0.18 | 1.87 | 1.81 | 34.55 | 27.08 |
| 209 | 4.92 | 0.19 | 3.49 | 1.87 | 29.13 | 26.05 |
| 210 | 5.65 | 0.18 | 3.50 | 1.83 | 29.13 | 30.75 |
| 212 | 4.66 | 0.19 | 2.82 | 1.87 | 30.98 | 24.77 |
| 213 | 4.56 | 0.18 | 1.33 | 1.79 | 37.50 | 25.18 |
| 214 | 5.13 | 0.18 | 1.93 | 1.82 | 34.28 | 28.11 |
| 215 | 4.79 | 0.18 | 3.23 | 1.82 | 29.82 | 26.20 |
| 217 | 4.68 | 0.18 | 1.49 | 1.83 | 36.57 | 25.56 |
| 219 | 5.19 | 0.19 | 1.60 | 1.77 | 35.91 | 26.84 |
| 220 | 5.19 | 0.19 | 2.74 | 1.75 | 31.23 | 27.24 |
| 221 | 5.47 | 0.18 | 3.04 | 1.83 | 30.34 | 29.68 |
| 222 | 5.51 | 0.19 | 5.08 | 1.89 | 25.88 | 29.01 |
| 223 | 5.36 | 0.19 | 2.17 | 1.76 | 33.29 | 28.12 |
| 228 | 5.21 | 0.19 | 2.67 | 1.85 | 31.46 | 28.10 |
| 230 | 5.53 | 0.18 | 2.52 | 1.78 | 31.98 | 30.75 |
| 231 | 5.78 | 0.18 | 3.31 | 1.80 | 29.61 | 31.94 |
| 232 | 5.93 | 0.18 | 5.47 | 1.80 | 25.25 | 32.66 |
| 233 | 4.92 | 0.18 | 1.64 | 1.78 | 35.70 | 27.57 |
| 234 | 5.54 | 0.18 | 2.64 | 1.78 | 31.57 | 30.94 |

TABLE 2

| | Invention | Article 1 | Article 2 | Article 3 |
|---|---|---|---|---|
| CR | 5.25 | 5.19 | 6.11* | 5.82* |
| PRD(%) | 0.19 | 0.23 | 0.78 | 0.8 |
| PRDN(%) | 2.88 | 3.56 | — | — |
| RMS | 1.81 | 2.22 | — | — |
| SNR | 31.45 | 29.67 | — | — |
| QS | 29.93 | 22.56 | 7.83 | 7.27 |

Although the present invention has been explained in relation to its preferred embodiment, it is to be understood that many other possible modifications and variations can be made without departing from the spirit and scope of the invention as hereinafter claimed.

What is claimed is:

1. An electrocardiogram signal compression system includes:
a normalization device for receiving N electrocardiogram signals and performing a normalization operation on the N electrocardiogram signals to generate N normalized signals, where N is a positive integer;

a discrete cosine transform device connected to the normalization device for receiving the N normalized signals and performing a discrete cosine operation to generate N discrete cosine signals;

an absolute value and quantization device connected to the discrete cosine transform device for receiving the N discrete cosine signals and performing an absolute value operation and a quantization operation to generate N quantized amplitude signals;

a difference coding device connected to the absolute value and quantization device for receiving the N quantized amplitude signals and performing differential pulse code modulation (DPCM) on the N quantized amplitude signals to generate N difference signals;

a first variable length coding device connected to the difference coding device for performing a first variable length coding operation on the N difference signals to generate a first data stream;

a sign and difference device connected to the discrete cosine transform device for receiving the N discrete cosine signals and recoding signs of the N discrete cosine signals, so as to generate three sign signals;

a second variable length coding device connected to the sign and difference device for performing a second variable length coding operation on the three sign signals to generate a second data stream; and a mixer connected to the first variable length coding device and the second variable length coding device for mixing the first data stream and the second data stream to generate a compressed electrocardiogram data stream.

2. The electrocardiogram signal compression system as claimed in claim 1, wherein the N electrocardiogram signals are respectively subtracted by $2^{K-1}$ and then divided by $2^{K-1}$ by the normalization device, so as to generate the N normalized signals, where K is a bit number of the N electrocardiogram signals.

3. The electrocardiogram signal compression system as claimed in claim 1, wherein the discrete cosine transform device is a type IV discrete cosine transform (DCT-IV) device.

4. The electrocardiogram signal compression system as claimed in claim 3, wherein the N discrete cosine signals are expressed by:

$$X[k] = \sum_{n=0}^{N-1} x(n) \times \cos\left(\frac{(2n+1)(2k+1)\pi}{4N}\right), n = 0, 1, \ldots, N-1,$$

where x(n) represents the normalized signals.

5. The electrocardiogram signal compression system as claimed in claim 4, wherein the absolute value and quantization device has a first quantization step and a second quantization step for performing the absolute value operation on the N discrete cosine signals to generate N absolute values of discrete cosine signals, and performing the quantization operation on the N absolute values of discrete cosine signals based on the first quantization step and the second quantization step, so as to generate the N quantized amplitude signals.

6. The electrocardiogram signal compression system as claimed in claim 5, wherein the first variable length coding device performs Huffman coding on the N difference signals to generate the first data stream.

7. The electrocardiogram signal compression system as claimed in claim 6, wherein the sign and difference device modifies part of the signs of the N discrete cosine signals so as to generate the three sign signals.

8. The electrocardiogram signal compression system as claimed in claim 7, wherein the second variable length coding device performs Huffman coding on the three sign signals to generate the second data stream.

9. An electrocardiogram signal de-compression system includes:

a parser device for receiving a compressed electrocardiogram data stream and analyzing the compressed electrocardiogram data stream, so as to generate a first data stream and a second data stream;

a first variable length decoding device connected to the parser device for performing a first variable length decoding operation on the first data stream to generate N difference signals, where N is a positive integer;

a difference decoding device connected to the first variable length decoding device for receiving the N difference signals and performing a differential pulse code modulation (DPCM) operation on the N difference signals to generate N quantized amplitude signals;

an inverse quantization device connected to the difference decoding device for receiving the N quantized amplitude signals and performing an inverse quantization operation to generate inverse quantization signals of N discrete cosine signals;

a second variable length decoding device connected to the parser device for performing a second variable length decoding operation on the second data stream to generate three sign and difference signals;

a restored difference and sign prediction device connected to the second variable length decoding device for receiving the three sign and difference signals and performing a restored difference and sign prediction operation to generate signs of the N discrete cosine signals;

an inverse discrete cosine transform device connected to the inverse quantization device and the restored difference and sign prediction device for receiving the inverse quantization signals of the N discrete cosine signals and the signs of the N discrete cosine signals to generate the N discrete cosine signals, and performing an inverse discrete cosine operation on the N discrete cosine signals so as to generate N normalized signals; and an inverse normalization device connected to the inverse discrete cosine transform device for receiving the N normalized signals and performing an inverse normalization operation on the N normalized signals to generate N electrocardiogram signals.

10. The electrocardiogram signal de-compression system as claimed in claim 9, wherein the first variable length decoding device performs Huffman decoding on the first data stream to generate the N difference signals.

11. The electrocardiogram signal de-compression system as claimed in claim 10, wherein the inverse quantization device has a first quantization step and a second quantization step for performing the inverse quantization operation on the N quantized amplitude signals based on the first quantization step and the second quantization step to generate the inverse quantization signals of the N discrete cosine signals.

12. The electrocardiogram signal de-compression system as claimed in claim 11, wherein the second variable length decoding device performs Huffman decoding on the second data stream to generate the three sign and difference signals.

13. The electrocardiogram signal de-compression system as claimed in claim 12, wherein the restored difference and sign prediction device subtracts a first constant from the first sign and difference signal, and adds a second constant to the second and third sign and difference signals, so as to generate first to third temporal signals, and further performs sign prediction on the first to third temporal signals to generate the signs of the N discrete cosine signals.

14. The electrocardiogram signal de-compression system as claimed in claim 13, wherein the inverse discrete cosine transform device is a type IV inverse discrete cosine transform (IDCT-IV) device.

15. The electrocardiogram signal de-compression system as claimed in claim 14, wherein the N normalized signals are expressed by:

$$x[n] = \frac{2}{N}\sum_{k=0}^{N-1} X[k] \times \cos\left(\frac{(2n+1)(2k+1)\pi}{4N}\right), k = 0, 1, ..., N-1,$$

where X[k] represents the N discrete cosine signals.

16. The electrocardiogram signal de-compression system as claimed in claim 15, wherein the N normalized signals are respectively multiplied by $2^{K-1}$ and then added with $2^{K-1}$ by the inverse normalization device, so as to generate the N electrocardiogram signals, where K is bit number of the N electrocardiogram signals.

* * * * *